(12) United States Patent
Murata et al.

(10) Patent No.: US 10,990,798 B2
(45) Date of Patent: Apr. 27, 2021

(54) ANALYSIS DEVICE, ANALYSIS METHOD, AND PROGRAM

(71) Applicants: THE UNIVERSITY OF TOKYO, Tokyo (JP); NIKON CORPORATION, Tokyo (JP)

(72) Inventors: Masayuki Murata, Tokyo (JP); Fumi Kano, Tokyo (JP); Yoshiyuki Noguchi, Tokyo (JP); Hirotada Watanabe, Yokohama (JP); Nobuhiko Maiya, Yokohama (JP); Shinichi Furuta, Yokohama (JP); Takuro Saigo, Tokyo (JP); Mamiko Masutani, Yokohama (JP); Masafumi Yamashita, Fujisawa (JP); Shoko Yamasaki, Tokyo (JP)

(73) Assignees: THE UNIVERSITY OF TOKYO, Tokyo (JP); NIKON CORPORATION, Tokyo (JP)

( * ) Notice: Subject to any disclaimer, the term of this patent is extended or adjusted under 35 U.S.C. 154(b) by 71 days.

(21) Appl. No.: 16/346,172

(22) PCT Filed: Nov. 10, 2016

(86) PCT No.: PCT/JP2016/083366
§ 371 (c)(1),
(2) Date: Apr. 30, 2019

(87) PCT Pub. No.: WO2018/087861
PCT Pub. Date: May 17, 2018

(65) Prior Publication Data
US 2020/0065556 A1 Feb. 27, 2020

(51) Int. Cl.
*G06K 9/00* (2006.01)
*G06K 9/52* (2006.01)
*G06T 7/00* (2017.01)

(52) U.S. Cl.
CPC .......... *G06K 9/00147* (2013.01); *G06K 9/52* (2013.01); *G06T 7/0012* (2013.01)

(58) Field of Classification Search
CPC ..... G06K 9/00147; G06K 9/52; G06T 7/0012
See application file for complete search history.

(56) References Cited

U.S. PATENT DOCUMENTS 8,606,809 B2 12/2013 Kato et al.
2006/0039593 A1* 2/2006 Sammak ............ G06K 9/00127
382/133

(Continued)

FOREIGN PATENT DOCUMENTS

EP 1672078 A1 6/2006
EP 2213722 A1 8/2010

(Continued)

OTHER PUBLICATIONS

Aug. 13, 2020 Search Report issued in European Patent Application No. 16921099.4.

(Continued)

*Primary Examiner* — Utpal D Shah
(74) *Attorney, Agent, or Firm* — Oliff PLC

(57) ABSTRACT

An analysis device includes: a cell image acquisition unit that acquires a plurality of cell images in which a stimulated cell has been captured; a feature value calculation unit that calculates a feature value for each of first and second constituent elements constituting the cell, from the cell images acquired by the cell image acquisition unit; a correlation calculation unit that calculates correlations between first feature values and between second feature values in the first and second constituent elements calculated by the feature value calculation unit; a correlation extraction unit that extracts the correlation between the first feature values by selecting the first feature values with respect to the correlations between the feature values in the first and (Continued)

second constituent elements calculated by the correlation calculation unit; and a display unit that displays the correlation between the first feature values extracted by the correlation extraction unit.

13 Claims, 8 Drawing Sheets

(56) References Cited

U.S. PATENT DOCUMENTS

| | | | | |
|---|---|---|---|---|
| 2006/0210962 | A1* | 9/2006 | Imaizumi | C12Q 1/04 435/4 |
| 2010/0274798 | A1 | 10/2010 | Kato et al. | |
| 2011/0228069 | A1* | 9/2011 | Mimura | G02B 21/0088 348/79 |
| 2012/0106822 | A1* | 5/2012 | Mimura | C12M 41/46 382/133 |
| 2013/0287283 | A1* | 10/2013 | Kamath | G06K 9/0014 382/133 |
| 2014/0099014 | A1* | 4/2014 | Kii | G06T 7/62 382/133 |
| 2014/0369587 | A1* | 12/2014 | Galloway | G02B 21/26 382/133 |
| 2016/0163044 | A1* | 6/2016 | Kunihiro | G01N 15/10 382/133 |
| 2017/0350805 | A1* | 12/2017 | Murata | C12M 1/34 |
| 2019/0266723 | A1* | 8/2019 | Blanchard | G01N 33/5026 |

FOREIGN PATENT DOCUMENTS

| | | |
|---|---|---|
| EP | 2444479 A1 | 4/2012 |
| EP | 3009501 A1 | 4/2016 |
| EP | 3239287 A1 | 11/2017 |
| JP | 2005-102538 A | 4/2005 |
| JP | 2009-063509 A | 3/2009 |
| WO | 2009/050886 A1 | 4/2009 |
| WO | 2010/146802 A1 | 12/2010 |
| WO | 2016/103501 A1 | 6/2016 |
| WO | WO-2018063914 A1 * | 4/2018 ......... G06K 9/00147 |

OTHER PUBLICATIONS

May 26, 2020 Office Action issued in Japanese Patent Application No. 2018-549693.
Feb. 14, 2017 International Search Report issued in International Patent Application No. PCT/JP2016/083366.
Feb. 14, 2017 Written Opinion issued in International Patent Application No. PCT/JP2016/083366.
Mar. 4, 2021 Office Action issued in European Patent Application No. 16921099.4.

* cited by examiner

ANALYSIS DEVICE, ANALYSIS METHOD, AND PROGRAM

TECHNICAL FIELD

Embodiments of the present invention relate to an analysis device, an analysis method, and a program.

BACKGROUND ART

In biological science, medical science and the like, it is known that there is a correlation, for example, between a state of health, disease, or the like; and a state of cells, organelles inside the cells, and the like. As a consequence, analyzing signaling pathways of information transmitted within cells or between cells can be helpful for research relating to biosensors in industrial applications, in the manufacture of drugs with the aim of preventing disease and the like. In various analysis techniques relating to cells and tissue slices, techniques that use image processing are known, for example (see Patent Document 1, for example).

CITATION LIST

Patent Documents

Patent Document 1: US 2014/00099014 A1

SUMMARY OF INVENTION

Technical Problem

However, when analyzing the correlation between feature values within a stimulated cell, the networks can become complex and lead to defective analyses.

Having been achieved in light of the above-described problem, an object of the present invention is to provide an analysis device, an analysis method, and a program.

Solution to Problem

One aspect of the present invention is an analysis device configured to analyze a correlation between feature values within a cell in response to a stimulus, the device including: a cell image acquisition unit configured to acquire a plurality of cell images in which the stimulated cell has been captured; a feature value calculation unit configured to calculate a feature value for each of the first and second constituent elements constituting the cell, from the cell images acquired by the cell image acquisition unit; a correlation calculation unit configured to calculate correlations between first feature values and between second feature values in the first and second constituent elements calculated by the feature value calculation unit; a correlation extraction unit configured to extract the correlation between the first feature values by selecting the first feature values with respect to the correlations between the feature values in the first and second constituent elements calculated by the correlation calculation unit; and a display unit configured to display the correlation between the first feature values extracted by the correlation extraction unit.

Another aspect of the present invention is an analysis device configured to analyze a correlation between feature values within a cell in response to a stimulus, the device including: a cell image acquisition unit configured to acquire a plurality of cell images in which the stimulated cell has been captured; a feature value calculation unit configured to calculate a feature value for constituent elements constituting the cell, from the cell images acquired by the cell image acquisition unit; a position information calculation unit configured to calculate the position information of the constituent elements calculated by the cell image acquisition unit; a correlation extraction unit configured to, by selecting the position information of the constituent elements, extract a correlation between the constituent elements pertaining to the selected position information; and a display unit configured to display the correlation of the constituent elements pertaining to the selected position information extracted by the correlation extraction unit.

Another aspect of the present invention is an analysis method executed by an analysis device configured to analyze a correlation between feature values within a cell in response to a stimulus, the method including: a step of acquiring a plurality of cell images in which the stimulated cell has been captured; a step of calculating a feature value for each of the first and second constituent elements constituting the cell, from the cell images acquired in the step of acquiring a plurality of cell images; a step of calculating correlations between first feature values and between second feature values in the first and second constituent elements calculated in the step of calculating the feature values; a step of extracting the correlation between the first feature values by selecting the first feature values with respect to the correlations between the feature values in the first and second constituent elements calculated in the step of calculating the correlations; and a step of displaying the correlation between the first feature values extracted in the step of extracting the correlation.

Another aspect of the present invention is an analysis method executed by an analysis device configured to analyze a correlation of feature values within a cell in response to a stimulus, the method comprising: a step of acquiring a plurality of cell images in which the stimulated cell has been captured; a step of calculating a feature value for constituent elements constituting the cell, from the cell images acquired in the step of acquiring a plurality of cell images; a step of calculating a correlation between constituent elements from the feature values of the constituent elements calculated in the step of calculating the feature values; a step of calculating the position information of the constituent elements calculated in the step of calculating the correlation; a step of selecting the position information of the constituent elements for which the position information has been calculated, to extract the correlation between the constituent elements pertaining to the selected position information; and a step of displaying the correlation of the constituent elements pertaining to the selected position information extracted in the step of extracting the correlation.

Another aspect of the present invention is a program configured to cause a computer of an analysis device to execute: a step of acquiring a plurality of cell images in which a stimulated cell has been captured; a step of calculating a feature value for each of the first and second constituent elements constituting the cell, from the cell images acquired in the step of acquiring a plurality of cell images; a step of calculating correlations between first feature values and between second feature values in the first and second constituent elements calculated in the step of calculating the feature values; a step of extracting the correlation between the first feature values by selecting the first feature values with respect to the correlations between the feature values in the first and second constituent elements calculated in the step of calculating the correlations;

and a step of displaying the correlation between the first feature values extracted in the step of extracting the correlation.

Another aspect of the present invention is a program configured to cause a computer of an analysis device to execute: a step of acquiring a plurality of cell images in which a stimulated cell has been captured; a step of calculating a feature value for constituent elements constituting the cell, from the cell images acquired in the step of acquiring a plurality of cell images; a step of calculating a correlation between constituent elements from the feature values of the constituent elements calculated in the step of calculating the feature values; a step of calculating the position information of the constituent elements calculated in the step of calculating the correlation; a step of selecting the position information of the constituent elements for which the position information has been calculated, to extract the correlation of the constituent elements pertaining to the selected position information; and a step of displaying the correlation of the constituent elements pertaining to the selected position information extracted in the step of extracting the correlation.

Advantageous Effects of Invention

According to embodiments of the present invention, a correlation between feature values within a cell in response to a stimulus can be analyzed.

DESCRIPTION OF EMBODIMENTS

Embodiment

Figure 1:
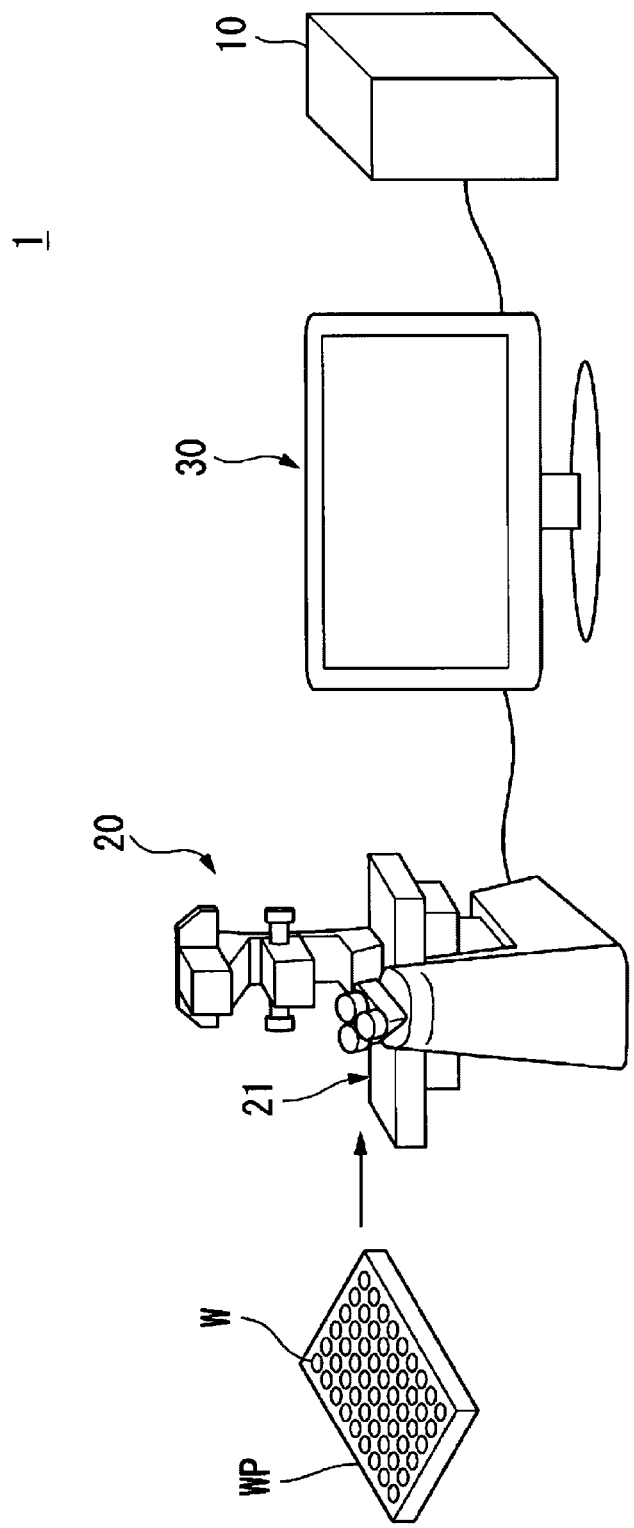
FIG. 1 is a schematic view illustrating one example of the configuration of a microscope observation system according to an embodiment.

An embodiment of the present invention will be described below with reference to the drawings. FIG. 1 is a schematic view illustrating one example of the configuration of a microscope observation system 1 according to an embodiment of the present invention.

The microscope observation system 1 performs analysis processing on an image acquired by capturing an image of cells or the like. In the following descriptions, the image acquired by capturing an image of cells or the like will be called simply a "cell image".

The microscope observation system 1 includes an analysis device 10, a microscope device 20, and a display unit 30.

The microscope device 20 is a biological microscope, and includes an electromotive stage 21 and an image capturing unit 22. The electromotive stage 21 can move an object to be imaged to a desired position in a predetermined direction (e.g., a direction within a horizontal two-dimensional plane). The image capturing unit 22 includes an image capturing element such as a CCD (Charge-Coupled Device), a CMOS (Complementary MOS), or a PMT (Photomultiplier Tube), and captures an image of the object to be imaged on the electromotive stage 21.

Note that the microscope device 20 does not need to include the electromotive stage 21, and the stage may be a stage that does not move in the predetermined direction.

To be more specific, the microscope device 20 has functions such as a differential interference contrast microscope (DIC), a phase contrast microscope, a fluorescence microscope, a confocal microscope, a super-resolution microscope, a two-photon excitation fluorescence microscope, a light sheet microscope, or a light field microscope, for example. The microscope device 20 captures an image of a culture vessel placed on the electromotive stage 21. This culture vessel is a well plate WP, a slide chamber, a Petri dish, or the like, for example.

The microscope device 20 irradiates cells cultivated inside wells W provided in the well plate WP, chambers provided in the chamber slide, or on a cover glass with light, and thus captures an image of transmitted light transmitted through the cells, as the image of the cells. In this way, an image of the cells can be acquired, such as a transmission DIC image, a phase contrast image, a dark field image, and a bright field image.

In addition, by irradiating the cells with excitation light that excites a fluorescent material, an image of fluorescence emitted from a biological material can be captured, as the image of the cells.

In the present embodiment, the cell image is acquired by staining the cells. In the present embodiment, the cells are stained while still alive, and a time lapse image is captured to acquire an image of changes in the cells after the cells have been stimulated. As yet another embodiment, the cells are immobilized and stained. When immobilizing the cells, the processing for immobilizing the cells is performed using a reagent such as formaldehyde. The metabolism of an immobilized cell stops. Thus, when observing changes within immobilized cells occurring over time, it is necessary to prepare cells seeded in a plurality of containers. For example, there are cases where one intends to observe changes in the cells over a first amount of time after the cells have been stimulated, and changes in the cells over a second amount of time different from the first amount of time. In this case, once the first amount of time has passed after the cells have been stimulated, the cells are immobilized, subjected to immunostaining, and the cell image is then acquired.

Meanwhile, a container with seeded cells, different from the container with seeded cells used in the observation during the first amount of time, is prepared, and the cells are stimulated. Then, after the second amount of time has passed, the cells are immobilized and subjected to immunostaining, and the cell image is then acquired. Through this, changes within the cells in response to stimuli can be estimated on the basis of the cell image from the first amount of time. Likewise, changes within the cells in response to stimuli can be estimated on the basis of the cell image from the second amount of time. Observing the changes in the cells in the first amount of time and the changes in the cells in the second amount of time makes it possible to estimate changes within the cells occurring over time. Additionally, the number of cells used for observing changes in the cells in the first amount of time and the second amount of time is not limited to 1. Thus, images of a plurality of cells are acquired in both the first amount of time and the second amount of time. For example, if the number of cells for observing changes within the cells is 1000, images of 2000 cells are captured in the first amount of time and the second amount of time, collectively. Thus, when attempting to acquire details of changes in cells occurring in response to stimuli, a plurality of cell images are necessary for each time spanning from the stimulus to the image being captured, and thus many cell images are acquired.

Alternatively, the microscope device 20 may capture, as the above-described image of the cells, an image of light or fluorescence emitted from the fluorescent material itself incorporated in a biological material, or of light or fluorescence produced when a material having chromophores combines with the biological material. In this way, the microscope observation system 1 can acquire a fluorescent picture image, a confocal image, a super-resolution image, or a two-photon excitation fluorescence microscopy image. Note that the method for acquiring an image of cells is not limited to optical microscopy. For example, the method for acquiring an image of cells may be electron microscopy.

For the cell images, images obtained through different methods may be used, and correlations may be found as well. That is, the type of the cell image may be selected as appropriate.

The cells in the present embodiment are, for example, primary cultured cells, subculture cells, cells from tissue sections, and the like. To observe the cells, an aggregate of cells, a tissue sample, an organ, or an individual (an animal or the like) may be used as a sample for observation, and an image including cells may be acquired.

Note that the state of the cells is not particularly limited, and the cells may be in a living state or may be in an immobilized state. The cells may be in an "in-vitro" state. Of course, information from a living state and information from an immobilized state may be combined.

The state of the cells may be selected as appropriate depending on the purpose. For example, an immobilized state or a non-immobilized state may be selected in accordance with the type of structural element in the cells to be determined (e.g., proteins or organelles).

When acquiring the dynamic behavior of cells using immobilized cells, immobilized cells are created with a plurality of different conditions, and the dynamic behavior is then acquired. The type of structure in the cell to be determined is not limited to the nucleus.

To observe the cells, the cells may be processed in advance and then observed. Of course, to observe the cells, the cells may be observed in an unprocessed state as well. When observing the cells, the cells may be stained through immunostaining and then observed.

With respect to the staining method, any staining method can be used. Various types of specific stains used primarily in tissue staining, hybridization using base sequence binding, and the like are examples.

Additionally, the cells may be processed with a light-emitting or fluorescent protein (e.g., a light-emitting or fluorescent protein expressed by introduced genes (a green fluorescent protein, GFP)) and then observed. For example, a light-emitting or fluorescent protein may be selected for the type of structure in the cells to be determined.

Alternatively, the observation may be carried out using a fluorescent dye (e.g., DAPI, Hoechst, or the like).

Additionally, means for observing the cells and preprocessing for analyzing correlation acquisitions, such as methods for staining the cells and the like, may be selected as appropriate in accordance with the purpose. For example, the dynamic information of the cells may be acquired through an optimum technique used when obtaining the dynamic behavior of cells, and information pertaining to intracellular signal transduction may be acquired through an optimum technique when intracellular signal transduction is to be acquired. The preprocessing that is selected may differ depending on the purpose. Additionally, the number of types of preprocessing that are selected may be reduced depending on the purpose. For example, if the technique for acquiring the dynamic behavior of the cells and the technique for acquiring the intracellular signal transduction have different optimum techniques, acquiring respective pieces of information using the respective different techniques is complicated. Thus, the same techniques, which are different from the optimum techniques, may be used in a case where doing so is sufficient for acquiring the respective pieces of information.

Additionally, the number of types of preprocessing that are selected may be reduced depending on the purpose. For example, if the technique for acquiring the dynamic behavior of the cells and the technique for acquiring the intracellular signal transduction have different optimum techniques, acquiring respective pieces of information using the respective different techniques is complicated. Thus, the same techniques, which are different from the optimum techniques, may be used in a case where doing so is sufficient for acquiring the respective pieces of information.

The well plate WP includes one or more wells W. As one example, the well plate WP includes 8×12, i.e. 96, wells W. The cells are cultivated in the wells W under specific experiment conditions. The specific experiment conditions include temperature, humidity, a cultivation period, an elapsed time period from when a stimulus is applied, a type and strength of the applied stimulus, a concentration, an amount, a presence or absence of a stimulus, inducing biological characteristics, and the like. The stimulus is, for example, a physical stimulus such as electricity, sound waves, magnetism, or light; or a chemical stimulus obtained by administering a substance, a drug or the like. The biological characteristics are characteristics that represent the stages of the differentiation of cells, morphology, the number of cells, the behavior of molecules in the cells, the morphology and behavior of organelles, the nuclear morphology, the behavior of the nuclear body, the behavior of the DNA molecules, and the like.

Figure 2:
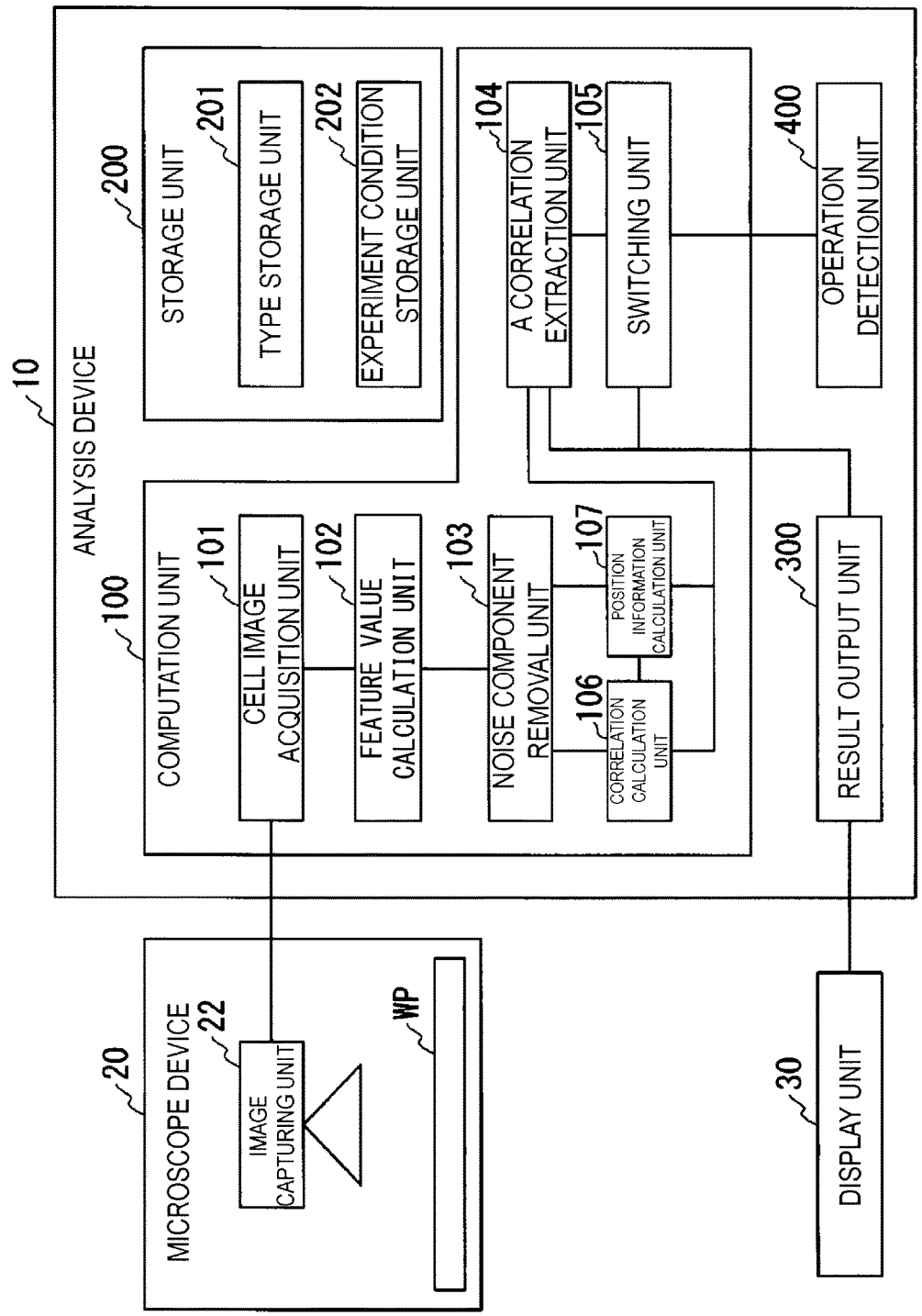
FIG. 2 is a block diagram illustrating one example of the functional configurations of each of the units included in an analysis device according to the embodiment.

FIG. 2 is a block diagram illustrating one example of the functional configurations of each of the units included in the analysis device 10 according to the present embodiment.

The analysis device 10 is a computer device that analyzes the image obtained by the microscope device 20. The analysis device 10 includes a computation unit 100, a storage unit 200, a result output unit 300, and an operation detection unit 400. Note that the images to be analyzed by the analysis device 10 are not limited to the images captured by the microscope device 20, and may be, for example, images stored in advance in the storage unit 200 included in the analysis device 10, or may be images stored in advance in an external storage device (not shown).

The computation unit 100 functions by a program stored in the storage unit 200 being executed by a processor. Some or all of each of these functional units of the computation unit 100 may be constituted by hardware, such as Large Scale Integration (LSI) or an Application Specific Integrated Circuit (ASIC).

The computation unit 100 includes a cell image acquisition unit 101, a feature value calculation unit 102, a noise component removal unit 103, a correlation extraction unit 104, a switching unit 105, a correlation calculation unit 106, and a position information calculation unit 107.

The cell image acquisition unit 101 acquires the cell images captured by the image capturing unit 22 and supplies the acquired cell images to the feature value calculation unit 102. The image acquired by the cell image acquisition unit 101 is not limited to an image captured by the image capturing unit 22. For example, if the cells have been cultivated, the image acquired by the cell image acquisition unit 101 may be an image of the cells during cultivation. In this case, different images taken in a time series during the cell cultivation may be included. For example, the cell image acquisition unit 101 acquires a plurality of cell images in which stimulated cells have been captured. Additionally, for example, the cell image acquisition unit 101 can acquire cell images in which different amounts of time have passed following the stimuli.

The feature value calculation unit 102 calculates one type or a plurality of types of feature values for each constituent element constituting the cells, from the cell images supplied by the cell image acquisition unit 101. The feature values of the cell image include, for example, the luminosity of the cell image, the surface area of the cells within the image, a variance in the luminosity of the cell images within the image, and the like. That is, the feature value of a cell image is information acquired from the captured cell image. For example, the feature value calculation unit 102 calculates a luminosity distribution within an acquired image. In the present embodiment, the feature value calculation unit 102 calculates a first feature value and a second feature value for each constituent element of the cells, as a plurality of types of feature values. The first feature value is luminosity values of the cell images, and the second feature value is a distribution of the luminosity values of the cell images within the image. The types of the first feature value and the second feature value calculated for each constituent element may be different.

The feature value calculation unit 102 acquires cell images in which different amounts of time have passed after stimuli have been applied to the cells. The feature value calculation unit 102 calculates feature values of the captured cells after a first amount of time has passed after stimuli have been applied to the cells. Furthermore, the feature value calculation unit 102 calculates feature values of the captured cells after a second amount of time has passed after stimuli have been applied to the cells. As a result, the feature value calculation unit 102 acquires images of the stimulated cells that are different in a time series. In the present embodiment, the cells used when capturing the image after the first amount of time has passed are different from the cells used when capturing the image after the second amount of time has passed. Note, however, that in the present embodiment, the cells used when capturing the image after the first amount of time has passed may be the same as the cells used when capturing the image after the second amount of time has passed.

In the present embodiment, the feature value calculation unit 102 acquires images with respect to the stimuli that are different in a time series and calculates changes over time in the feature values in the time series. However, the present embodiment is not limited thereto. For example, the feature value calculation unit 102 may use a fixed amount of time following the application of a stimulus, vary the magnitude of the applied stimulus, and then calculate changes in the feature value occurring in response to the variation of the magnitude of the stimulus. The feature value calculation unit 102 calculates changes in the feature value from the acquired image. The feature value calculation unit 102 may use a luminosity distribution and the position information of the luminosity distribution as the feature value. Additionally, when changes cannot be confirmed from the captured cell images, the feature value calculation unit 102 may treat the lack of changes as a change in the feature value.

The noise component removal unit 103 removes noise components (noise) from the feature values calculated by the feature value calculation unit 102.

The correlation calculation unit 106 calculates correlations between a plurality of types of feature values among the constituent elements, from the plurality of types of feature values for each of the constituent elements. The correlation calculation unit 106 calculates the correlations between the feature values among the constituent elements using the feature values from which the noise components have been removed by the noise component removal unit 103. Additionally, the correlation calculation unit 106 calculates correlations between constituent elements from the feature values for each of the constituent elements. The correlation calculation unit 106 calculates a correlation between the feature value of a first constituent element and the feature value of a second constituent element. Accordingly, the correlation calculation unit 106 calculates a correlation between the first feature value of the first constituent element and the first feature value of the second constituent element. For example, the correlation calculation unit 106 calculates the presence or absence of a correlation between a change in the first feature value of the first constituent element after a stimulus has been applied and a change in the second feature value of the second constituent element after a stimulus has been applied. Likewise, the correlation calculation unit 106 calculates a correlation between the second feature value of the first constituent element and the second feature value of the second constituent element. Accordingly, the correlation calculation unit 106 calculates a correlation between the first feature values of the first constituent element and the second constituent element. Additionally, the correlation calculation unit 106 calculates a correlation between the second feature values of the first constituent element and the second constituent element. In the present embodiment, the calculation of the correlation calculation unit 106 indicates that there is a correlation between the first and second feature values in the first and second constituent elements. The position information calculation unit 107 calculates the position information of the constituent element calculated by the correlation calculation unit 106. Note that the position information calculation unit 107 may use the position information of the constituent element calculated by the cell image acquisition unit 101.

The correlation extraction unit 104 selects a type of feature value with respect to the correlation between a plurality of types of feature values among the constituent elements, calculated by the correlation calculation unit 106, to extract a correlation for the type of feature value that has been selected. For example, when correlations between the first feature values and between the second feature values are calculated between the first constituent element and the second constituent element, selecting the first feature value results in the correlation between the first feature values being extracted. Additionally, the correlation extraction unit 104 selects the position information of the constituent elements to extract a correlation for the constituent elements having the selected position information.

The result output unit 300 outputs computation results from the computation unit 100, networks that have changed, and the like to the display unit 30. For example, the result output unit 300 displays the correlation between feature values extracted by the correlation extraction unit 104. Additionally, the result output unit 300 displays the correlation between constituent elements in the position information extracted by the correlation extraction unit 104. Note that the result output unit 300 may output computation results from the computation unit 100, networks created from correlation information, and the like to an output device aside from the display unit 30, a storage device, or the like.

The operation detection unit 400 detects an operation made on the analysis device 10 and supplies an operation signal representing the operation to the switching unit 105 of the computation unit 100.

The switching unit 105 switches the display of correlations between feature values. For example, after a correlation, such as between feature values, between constituent elements in position information, or the like, has been output to the display unit 30 by the result output unit 300, the switching unit 105 switches the correlation, such as between feature values, between constituent elements in position information, or the like, in accordance with an operation signal supplied to the operation detection unit 400. For example, the switching unit 105 switches one or both of the granularity of the correlation between specific feature values and the fineness of a region where a feature value having a specific correlation is located. "Granularity" refers to the number of edges constituting a network, which indicates the correlation between feature values. Thus, in the present embodiment, the number of edges, which indicate the correlation between feature values, can be varied. Varying the number of edges makes it possible to concretely or abstractly express the correlation between feature values. The switching unit 105 outputs the network, obtained as a result of the switching, to the result output unit 300.

The display unit 30 displays the computation result output by the result output unit 300.

The specific computation procedure carried out by the computation unit 100 described above will now be described with reference to FIG. 3.

Figure 3:
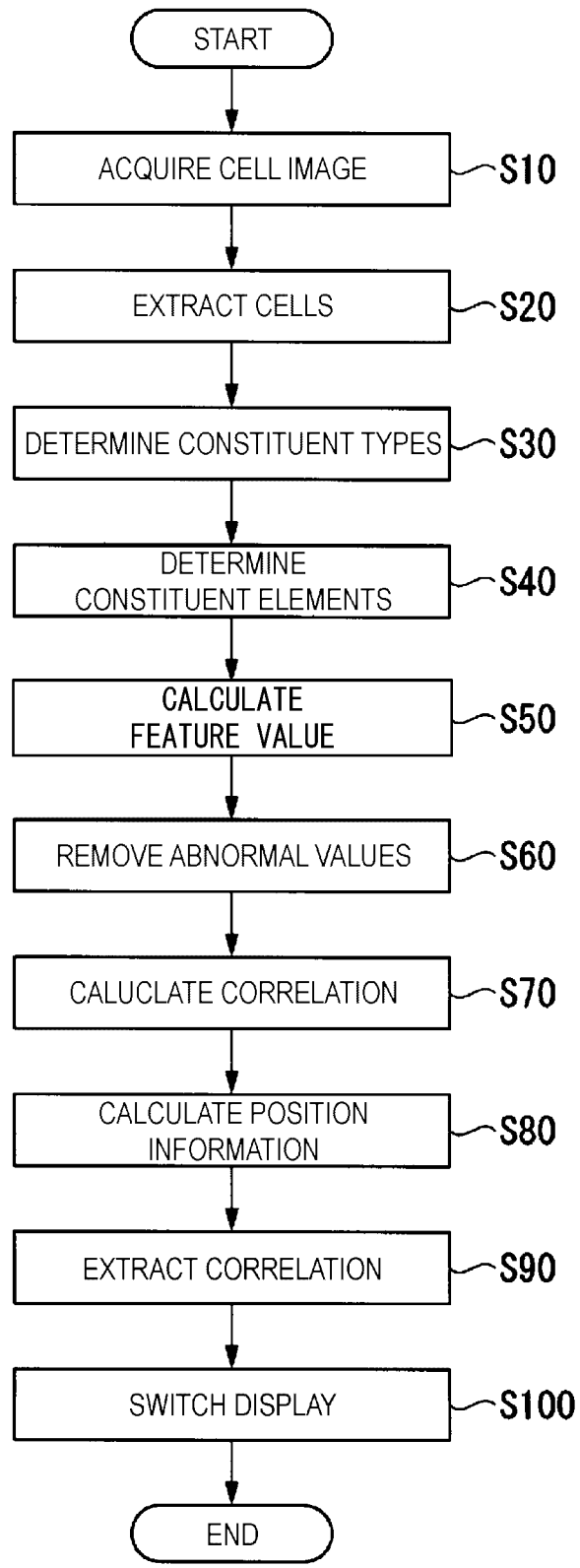
FIG. 3 is a flowchart illustrating one example of a computation procedure of a computation unit in the analysis device according to the embodiment.

FIG. 3 is a flowchart illustrating one example of the computation procedure performed by the computation unit 100. Note that the computation procedure illustrated here is merely one example, and some portions of the computation procedure may be omitted or added. Using the cell images in which images of cells have been captured, the computation unit 100 extracts a plurality of types of feature values in the cell images, and computes whether changes in the respective extracted feature values are correlated. That is, the computation unit 100 calculates a correlation with respect to changes in predetermined feature values. The computation unit 100 determines that there is a correlation when the calculation result indicates that the changes in the feature values are correlated. Note that a correlation between the feature values may be referred to as a "correlation relationship".

The cell image acquisition unit 101 acquires the cell images (step S10). The cell images include images of a plurality of types of biological tissues having different sizes, such as genes, proteins, organelles, and the like. For example, the cell image acquisition unit 101 acquires a plurality of cell images in which stimulated cells have been captured. The cell image acquisition unit 101, which acquires images using the image capturing unit 22, extracts a region corresponding to a cell from the image. For example, the cell image acquisition unit 101 extracts a region corresponding to a cell by extracting contours from the cell image. Accordingly, the region corresponding to the cell can be distinguished from other regions on the basis of the captured image.

The shape information of the cell is also included in the cell image.

The feature value calculation unit 102 extracts an image of each of the cells included in the cell image acquired in step S10 (step S20). The feature value calculation unit 102 extracts images of the cells by subjecting the cell image to image processing using a known method. In this example, the feature value calculation unit 102 extracts the images of the cells using contour extraction, pattern matching, or the like on the image.

Next, the feature value calculation unit 102 determines the type of the cell for the image of the cell extracted in step S20 (step S30).

Furthermore, the feature value calculation unit 102 determines constituent elements of the cell included in the image of the cell extracted in step S20, on the basis of the determination result from step S30 (step S40). Here, the constituent elements of the cell include cell organelles such as the cell nucleus, lysosome, Golgi apparatus, mitochondria, and the like; proteins, second messengers, mRNA, metabolites, nuclear bodies, genes, and the like. Note that in the present embodiment, if there is only a single cell to be used, the feature value calculation unit 102 does not need to determine the type of the cell. For example, the feature value calculation unit 102 may find the type of the cell from the contour information of the captured image. Additionally, in the case where the type of the cell to be introduced is known in advance, the feature value calculation unit 102 may specify the type of the cell using that information. Of course, it is also possible to not specify the type of the cell.

Next, the feature value calculation unit 102 calculates feature values for each of the constituent elements of the cell specified in step S40 (step S50). These feature values include luminosity values of pixels, the area of a region within the image, a variance in luminosity values of the pixels, the shape of a region within the image, and the like. When luminosity values of the pixels are used as the feature value, luminosity values for each of the wavelengths may be used as the feature value. A plurality of types of feature values may be used depending on the constituent element of the cell. As one example, the feature values in images of the cell nucleus include an overall intra-nuclear luminosity value, the area of the nucleus, the shape of the nucleus, and the like. Feature values of an image of cytoplasm include an overall intra-cytoplasm luminosity value, the area of the cytoplasm, the shape of the cytoplasm, and the like. Additionally, feature values of an image of the overall cell include an overall intra-cell luminosity value, the area of the cell, the shape of the cell, and the like. Feature values of an image of the mitochondria include a fragmentation rate.

Note that the feature value calculation unit 102 may make the calculations by normalizing values of the feature values from 0 (zero) to 1, for example.

The feature value calculation unit 102 may calculate feature values on the basis of the information of conditions of experiments on cells associated with the cell images. For example, when a cell image has been captured with the cells having reacted with antibodies, the feature value calculation unit 102 may calculate feature values unique to a case where a reaction has been produced with antibodies. Meanwhile, if the cell image has been captured with the cells having been stained or with a fluorescent protein having been added to the cells, the feature value calculation unit 102 may calculate unique feature values for the cases where the cells have been stained or a fluorescent protein has been added to the cells.

In these cases, the storage unit 200 may include an experiment condition storage unit 202. The information of the experiment conditions for the cells associated with the cell image is stored in the experiment condition storage unit 202, for each of the cell images. The feature value calculation unit 102 supplies the feature values calculated in step S50 to the noise component removal unit 103.

The noise component removal unit 103 removes a noise component from the feature values calculated in step S50 (step S60). Specifically, the noise component removal unit 103 acquires information indicating a normal range or an abnormal range for the feature value. The information indicating the normal range or the abnormal range of the feature value is determined in advance on the basis of characteristics of the cells captured in the cell image. For example, of feature values of an image of the cell nucleus, a normal range for the overall intra-nuclear luminosity value is determined on the basis of characteristics of the image of the cell nucleus.

If the calculated feature value does not fall within the normal range, the noise component removal unit 103 extracts that feature value as a noise component. Here, when removing a feature value as a noise component, the noise component removal unit 103 carries out the removal for each cell. Specifically, a plurality of feature values are sometimes calculated for a given cell.

For example, an overall intra-cell luminosity value, an overall intra-nuclear luminosity value, the area of the nucleus, and the shape of the nucleus may each be calculated as feature values for a given cell. In this case, when removing the overall intra-cell luminosity value as a noise component for the given cell, the noise component removal unit 103 also removes the overall intra-nuclear luminosity value, the area of the nucleus, and the shape of the nucleus for that cell. In other words, when at least one of the plurality of feature values calculated for a given cell does not fall within the normal range, the noise component removal unit 103 also removes the other feature values for that cell.

That is, the noise component removal unit 103 removes the noise components from the feature values to be supplied to the correlation calculation unit 106, for each cell captured in the cell image, on the basis of the information indicating characteristics of the cells captured in the cell image. By using this configuration, when there is a feature value that is relatively unreliable, the noise component removal unit 103 can remove that feature value on a cell-by-cell basis. In other words, the noise component removal unit 103 can improve the reliability of the feature values.

On the other hand, when the calculated feature value falls within the normal range, the noise component removal unit 103 supplies that feature value to the correlation calculation unit 106. Note, however, that the noise component removal unit 103 is not a necessary constituent element, and can be omitted depending on the state of the cell images, the state of the calculation of the feature values, and the like.

On the basis of one or more types of feature values for each constituent element, the correlation calculation unit 106 calculates correlations between the one or more types of feature values among the constituent elements (step S70).

The position information calculation unit 107 calculates the position information of the constituent elements calculated by the correlation calculation unit 106 (step S80).

The correlation extraction unit 104 selects a type of feature value with respect to the correlation between a plurality of types of feature values among the constituent elements, calculated by the correlation calculation unit 106, to extract a correlation for the type of feature value that has been selected. Additionally, the correlation extraction unit 104 selects the position information of the constituent elements to extract a correlation for the constituent elements having the selected position information (step S90).

The correlation extraction unit 104 extracts some of the correlations among the correlations calculated by the correlation calculation unit 106.

The processing performed by the correlation extraction unit 104 will be described in more detail below.

The feature value calculation unit 102 calculates a plurality of feature values for a protein 1, on a cell-by-cell basis and on a time-by-time basis. The feature value calculation unit 102 calculates feature values for N cells, from a cell 1 to a cell N. Additionally, the feature value calculation unit 102 calculates feature values for T points in time, from time 1 to time T. Additionally, the feature value calculation unit 102 calculates K types of feature values, from a feature value k1 to a feature value kK (where K is an integer in which K>0). In other words, the feature value calculation unit 102 calculates a plurality of feature values, at each time and for each protein in each cell.

The correlation extraction unit 104 selects a specific type of feature value with respect to the correlation between a plurality of types of feature values among the constituent elements, calculated by the correlation calculation unit 106, to extract a correlation for the type of feature value that has been selected. Here, the specific correlation of the feature values may be a correlation selected from among a plurality of correlations between feature values using a mathematical computation. The number of specific correlations of feature values is lower than the number of the plurality of correlations between feature values before being extracted by the correlation extraction unit 104.

One example of the specific correlation according to the present embodiment will be described in detail next. In the following, proteins will be referred to as "nodes". Additionally, constituent elements (structures) within the cell where nodes are present, such as organelles, will be referred to as "regions" (position information). Cell organelles such as the cell nucleus, lysosomes, Golgi apparatus, mitochondria, and the like, that is, constituent elements such as organelles within the cell, can be "nodes" as well as "regions". Networks of structures within the cells are represented by a plurality of nodes being connected by edges.

Figure 4:
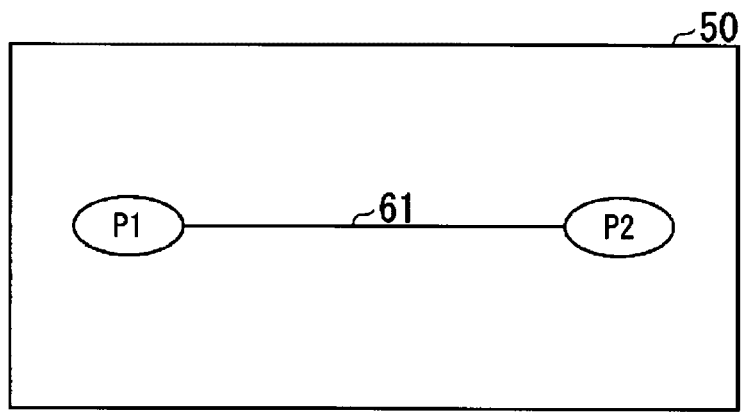
FIG. 4 is a diagram illustrating one example of a network of structures within a cell, output by the analysis device according to the embodiment.

FIG. 4 illustrates one example of a network of structures within a cell. In the example illustrated in FIG. 4, the correlation between the feature value of a node P1 and the feature value of a node P2 at a region 50 is represented by a connection made by an edge 61.

In the present embodiment, the entire network within the cell is displayed while the correlation between the feature value of the node P1 and the feature value of the node P2 is connected by the edge 61. Accordingly, the network can be compared to "pathways", which have been publicized in KEGG (Kyoto Encyclopedia of Genes and Genomes) and the like.

Figure 5:
FIG. 5 is a diagram illustrating one example of a relationship between edges and feature values of nodes connected by the edges.
Figure 5:
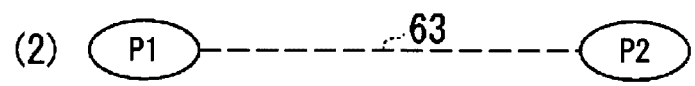
Figure 5:
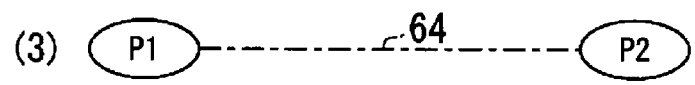

FIG. 5 is a diagram illustrating one example of a relationship between edges and feature values of nodes connected by the edges. As described above, the feature values include the luminosity, area, variance, shape, and the like in the cell image. It is possible to confirm what feature value the nodes connected by an edge pertain to, and thus biological indicators can be obtained.

FIG. 5 (1) indicates that the shape of the node P1 and the shape of the node P2 are connected by an edge 62, which is represented by a solid line. The shape is related to protein agglutination, and there is thus an indication that a node P3, related to the agglutination of the node P1 and the agglutination of the node P2, may be present.

FIG. 5 (2) indicates that the shape of the node P1 and the luminosity of the node P2 are connected by an edge 63, which is represented by a broken line. The shape is related to protein agglutination, whereas the luminosity is related to protein concentration, and thus there is an indication that the concentration of the node P2 may cause agglutination of the node P1.

FIG. 5 (3) indicates that the luminosity of the node P1 and the luminosity of the node P2 are connected by an edge 64, which is represented by a dot-dash line. Luminosity is related to protein concentration, and there is thus an indication that a node P3, related to the concentration of the node P1 and the concentration of the node P2, may be present.

Although FIG. 5 illustrates an example in which the shape of the node P1 and the shape of the node P2 are connected, the shape of the node P1 and the luminosity of the node P2 are connected, and the luminosity of the node P1 and the luminosity of the node P2 are connected, the connections are not limited to this example.

For example, the shape of the node P1 and the variance of the node P2 may be connected, the luminosity of the node P1 and the shape of the node P2 may be connected, and the luminosity of the node P1 and the variance of the node P2 may be connected. Additionally, for example, the variance of the node P1 and the shape of the node P2 may be connected, the variance of the node P1 and the luminosity of the node P2 may be connected, and the variance of the node P1 and the variance of the node P2 may be connected.

In other words, the correlations between feature values are connected by edges, for all of the combinations of feature values of the node P1 and feature values of the node P2, that is, nine types of combinations.

Furthermore, the magnitude of the value of the correlation between a plurality of nodes may be displayed as the length of the edge connecting the plurality of nodes, or may be represented by the thickness of the edge. Here, the value of the correlation among a plurality of nodes can be calculated by any desired method. For example, when the value of the correlation among a plurality of nodes is represented by the thickness of the edge connecting the plurality of nodes, the edge may be made thicker as the correlation value increases, and the edge may be made thinner as the correlation value decreases.

Figure 6:
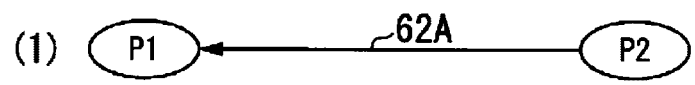
FIG. 6 is a diagram illustrating one example of types of edges.
Figure 6:
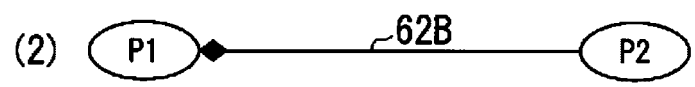

FIG. 6 is a diagram illustrating one example of types of edges. The edge types include "progressive" and "regressive". If, when the feature value of one of the nodes changes from a steady state and the other feature value changes from a steady state, the nodes are connected by an edge indicated as "progressive". Hereinafter, one of the nodes connected by an edge indicated as progressive will be called a "progress origin", and the other node a "progress destination".

Additionally, if, when the feature value of one of the nodes changes from a steady state and the other feature value returns to a steady state, the nodes are connected by an edge indicated as "regressive". Hereinafter, one of the nodes connected by an edge indicated as regressive will be called a "regression origin", and the other node a "regression destination". Thus, the edge may indicate a causal relationship (an edge having an orientation) instead of a correlation.

Note that if, when the feature value of one of a plurality of nodes increases and the feature values of the other nodes increase, the nodes may be connected by an edge indicated as "progressive". Additionally, if, when the feature value of one of a plurality of nodes increases and the feature value of the other node decreases, the nodes may be connected by an edge indicated as "regressive".

FIG. 6 (1) indicates that the shape of the node P1 and the shape of the node P2 are connected by an edge 62A, which is represented by a solid line having an arrow pointing from the node P2 toward the node P1. This indicates that when the feature value of the node P2 changes from the steady state, the feature value of the node P1 changes from the steady state.

FIG. 6 (2) indicates that the shape of the node P1 and the shape of the node P2 are connected by an edge 62B, indicated by a solid line having a diamond shape on the node P1 side. This indicates that when the feature value of the node P2 changes from the steady state, the feature value of the node P1 returns to the steady state.

Although FIG. 6 indicates the combination of the shape of the node P1 and the shape of the node P2 as being progressive or regressive, combinations are not limited to this example. For example, an edge indicated as progressive or an edge indicated as regressive can be indicated on the basis of the correlation between the feature values for all combinations of the feature value of the node P1 and the feature value of the node P2.

The switching unit 105 switches the display of the correlation between the feature values extracted in step S90, the position information, and the like (step S100). Specifically, the switching unit 105 switches the display of the correlation between the feature values, the position information, and the like in accordance with an operation signal supplied by the operation detection unit 400. The processing carried out by the switching unit 105 will be described in detail below.

Figure 7:
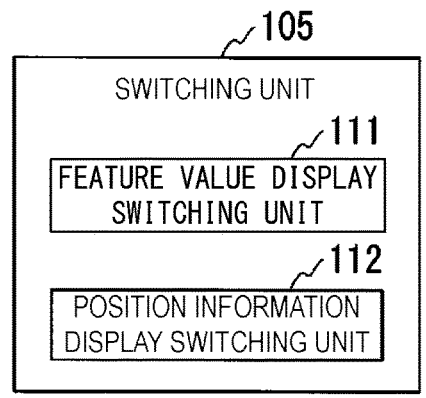
FIG. 7 is a block diagram illustrating one example of the functional configuration of a switching unit included in the analysis device according to the embodiment.

FIG. 7 is a block diagram illustrating one example of the functional configuration of the switching unit 105 according to the present embodiment. The switching unit 105 includes a feature value display switching unit 111 and a position information display switching unit 112.

The feature value display switching unit 111 switches the edge connecting a plurality of nodes in accordance with an operation signal supplied by the operation detection unit 400. This makes it possible to compare the network with KEGG.

<Edge Consolidation>

When a single correlation indicates a plurality of correlations among feature values, the feature value display switching unit 111 switches the display of the single correlation to the plurality of correlations among the feature values. That is, when there are plurality of edges connecting the feature values of two nodes, the feature value display switching unit 111 consolidates the edges. Here, the feature values having a correlation between the two nodes connected by the edges to be consolidated may be the same, or may be different.

Furthermore, when there are a plurality of edges indicated as progressive connecting two nodes, the feature value display switching unit 111 may consolidate the plurality of edges indicated as progressive. In this case, the feature value display switching unit 111 may consolidate edges in which the progress origin and the progress destination are the same, that is, edges having an equivalent orientation.

Additionally, when there are a plurality of edges indicated as regressive connecting two nodes, the feature value display switching unit 111 may consolidate the plurality of edges indicated as regressive. In this case, the feature value display switching unit 111 may consolidate edges in which the regression origin and the regression destination are the same, that is, edges having an equivalent orientation.

Additionally, when there are a plurality of edges connecting two nodes, and the plurality of edges include edges having a positive correlation value and edges having a negative correlation value, the feature value display switching unit 111 may consolidate the edges having a positive correlation value separate from the edges having a negative correlation value.

<Edge Separation>

Additionally, when a plurality of correlations among feature values are indicated, the feature value display switching unit 111 switches the display from the plurality of correlations among the feature values to a single correlation. That is, when an edge connecting two nodes is a plurality of edges that have been consolidated, the feature value display switching unit 111 separates those edges for each combination of feature values. Here, the feature values having a correlation between the two nodes connected by the edges to be separated may be the same, or may be different.

Additionally, when an edge connecting two nodes is a plurality of edges that have been consolidated, the feature value display switching unit 111 may separate those edges into edges indicated as progressive and edges indicated as regressive. In this case, the feature value display switching unit 111 may separate the edges into edges having equivalent orientations.

Additionally, when an edge present in a specific region is a consolidation of a plurality of edges, the feature value display switching unit 111 may separate those edges. Additionally, when an edge connecting specific nodes is a consolidation of a plurality of edges, the feature value display switching unit 111 may separate those edges.

<Edge Erasure and Addition>

The feature value display switching unit 111 erases a correlation between feature values. That is, the feature value display switching unit 111 erases an edge connecting two nodes. For example, the feature value display switching unit 111 erases an edge representing the correlation of the feature values of two nodes, the value of which is less than the predetermined threshold, and an edge representing the correlation of the feature values, the value of which is lower, in a predetermined order, from the highest value.

Additionally, the feature value display switching unit 111 erases an edge for which the structures within the cell indicating two nodes are equivalent, an edge connected to a node unrelated to a pre-set node, and an edge representing a correlation among pre-set feature values. Additionally, the feature value display switching unit 111 may change a correlation coefficient.

The feature value display switching unit 111 may display the correlation between feature values that has been erased.

A specific example of the processing carried out by the feature value display switching unit 111 will be described in detail below.

Figure 8:
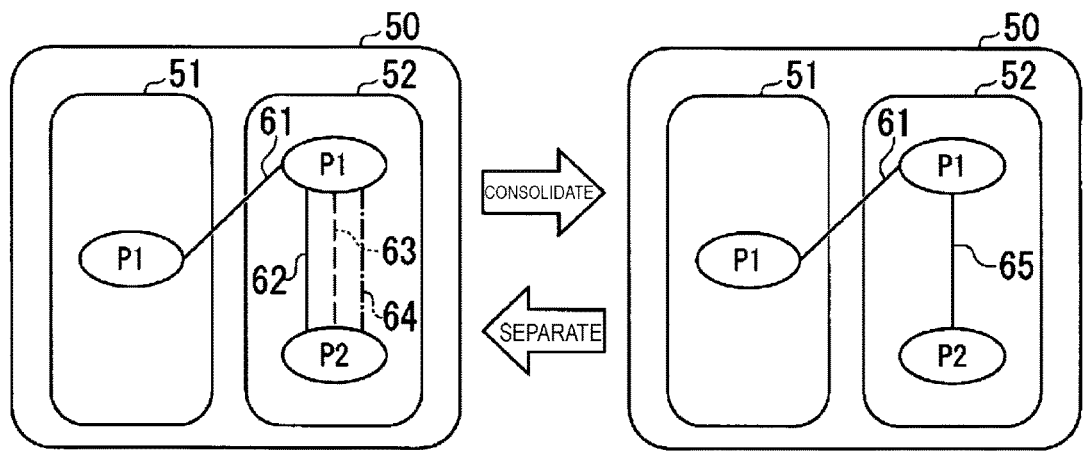
FIG. 8 is a diagram illustrating one example of a network (no. 1) of structures within a cell, output by the analysis device according to the embodiment.

FIG. 8 illustrates one example (no. 1) of a network of structures within a cell.

The left part of FIG. 8 indicates that a region 51 and a region 52 are present within the region 50, that the node P1 is present in the region 51, and that the node P1 and the node P2 are present in the region 52. Furthermore, the node P1 present in the region 51 and the node P1 present in the region 52 are connected by the edge 61, and the node P1 and the node P2 present in the region 52 are connected by the edge 62, the edge 63, and an edge 64.

The right part of FIG. 8 indicates the result of connecting the node P1 and the node P2 present in the region 52, in the left part of FIG. 8, by an edge 65.

For example, a case will be described where an operation for confirming the bold edge, specifically, an operation for consolidating the edge 62, the edge 63, and the edge 64, has been made in the analysis device 10 in a state where the network in the left part of FIG. 8 is displayed in the display unit 30.

An operation signal representing the consolidation operation is detected by the operation detection unit 400 and supplied to the feature value display switching unit 111 of the switching unit 105. Upon being supplied with the operation signal, the feature value display switching unit 111 acquires the correlation between feature values of the network displayed in the display unit 30. Then, in accordance with the operation signal, the feature value display switching unit 111 switches the granularity of the correlation between the feature values. Specifically, the feature value display switching unit 111 consolidates a plurality of correlations between specific feature values into a single correlation. For example, the node P1 and the node P2 present in the region 52 are connected by the edge 65, which is a consolidation of the edge 62, the edge 63, and the edge 64, and as a result, switching to the network indicated in the right part of FIG. 8. This makes it possible to reduce the number of networks connecting P1 and P2.

Here, the feature value display switching unit 111 may carry out statistical processing using the value of the correlation between the feature values of the nodes connected by the edge 62; the value of the correlation between the feature values of the nodes connected by the edge 63; and the value of the correlation between the feature values of the nodes connected by the edge 64, and then may display a statistical value obtained through the statistical processing in the vicinity of the edge 65, or change the thickness of the edge 65 in accordance with the statistical value.

For example, the feature value display switching unit 111 may find a total value, or may find an average value, of the value of the correlation between the feature values of the nodes connected by the edge 62; the value of the correlation between the feature values of the nodes connected by the edge 63; and the value of the correlation between the feature values of the nodes connected by the edge 64. At this time, the feature value display switching unit 111 may also carry out a statistical calculation using absolute values of the correlation values.

Additionally, the feature value display switching unit 111 may select the maximum value among the value of the correlation between the feature values of the nodes connected by the edge 62, the value of the correlation between the feature values of the nodes connected by the edge 63, and the value of the correlation between the feature values of the nodes connected by the edge 64, and then display the selected maximum value in the vicinity of the edge 65, or change the thickness of the edge 65 in accordance with the selected maximum value. At this time, the feature value display switching unit 111 may also carry out a statistical calculation using the absolute values of the correlation values.

Additionally, the feature value display switching unit 111 may change the thickness of the edge 65 in accordance with the number of edges between the node P1 and the node P2 relative to the total number of combinations of the number of feature values of the node P1 and the number of feature values of the node P2. Hereinafter, the number of edges indicating a high correlation between the node P1 and the node P2 relative to the total number of combinations of the number of feature values of the node P1 and the number of feature values of the node P2 will be referred to as a "high correlation rate".

Figure 9:
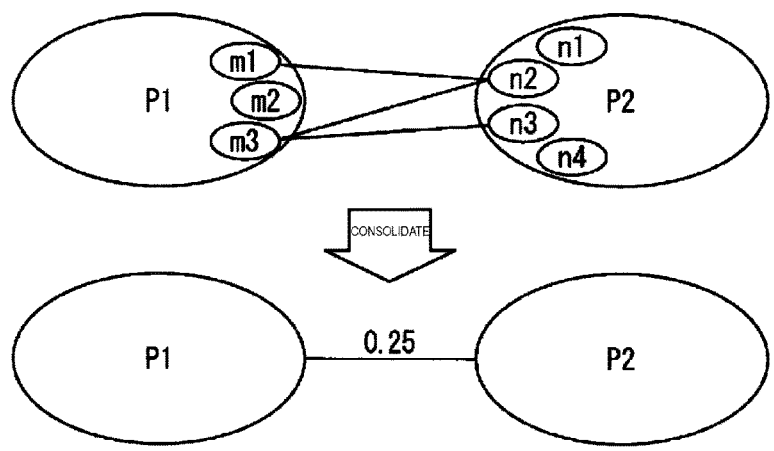
FIG. 9 is a diagram illustrating an example of the calculation of a high correlation rate between a node P1 and a node P2.

FIG. 9 is a diagram illustrating an example of the calculation of the high correlation rate between the node P1 and the node P2. In FIG. 9, m1, m2, and m3 within the node P1 indicate feature values of the node P1, and n1, n2, n3, and n4 within the node P2 indicate feature values of the node P2.

In the upper part of FIG. 9, the feature value m1 and the feature value n2 are connected at a high correlation rate, the feature value m3 and the feature value n2 are connected at a high correlation rate, and the feature value m3 and the feature value n3 are connected at a high correlation rate. That is, there are three edges indicating a high correlation connecting feature values of the node P1 and feature values of the node P2.

Here, the total number of combinations of edges between the node P1 and the node P2 is calculated as a product of the number of feature values of the node P1 and the number of feature values of the node P2. That is, the total number of combinations of edges between the node P1 and the node P2 is 3×4=12. Thus, the high correlation rate is 3/12=0.25. In the bottom part of FIG. 9, when the correlation value is represented by an edge percentage, the correlation value becomes 0.25 when the edges in the upper part of FIG. 9 are consolidated. Although the edges connecting the feature values of the node P1 and the feature values of the node P2 indicate high correlations, the edges may be indicated regardless of whether the correlation is high or low. The feature value display switching unit 111 may recognize instances of correlation between the feature values m1, m2, and m3 of the node P1 and the feature values n1, n2, and n3 of the node P2 as edges. In this case, when, for example, there are edges between m1 and n2, between m3 and n2, and between m3 and n3 as in FIG. 9, the feature value display switching unit 111 finds that of the total number of edge combinations, which is 3×4=12, edges are only present for 3/12=0.25. In this case, the feature value display switching unit 111 can calculate the ratio of correlated edges to edges that can be correlated as the edge percentage.

The feature value display switching unit 111 outputs information indicating that the granularity of the correlation between specific feature values has been switched to the result output unit 300. On the basis of the information supplied from the feature value display switching unit 111, indicating that the granularity of the correlation between specific feature values has been switched, the result output unit 300 displays the network indicated in the right side of FIG. 8 in the display unit 30.

The edge 65 is displayed at a thickness based on the value of the correlation between the nodes connected by the edge 62, the value of the correlation between the nodes connected by the edge 63, and the value of the correlation between the nodes connected by the edge 64, and thus the user can confirm the value of the correlation between the node P1 and the node P2 by the thickness of the edge.

The descriptions will be continued, returning to FIG. 8. A case will be described where, for example, an operation for confirming the feature values, specifically, an operation for separating the edge 65, has been made in the analysis device 10 in a state where the network in the right part of FIG. 8 is displayed in the display unit 30.

An operation signal representing the separation operation is detected by the operation detection unit 400 and supplied to the feature value display switching unit 111 of the switching unit 105.

Upon detecting the operation signal, the feature value display switching unit 111 acquires the correlation between feature values of the network displayed in the display unit 30. Then, in accordance with the operation signal, the feature value display switching unit 111 switches the granularity of the correlation between the feature values. Specifically, the feature value display switching unit 111 separates the correlation between specific feature values into a plurality of correlations. For example, the feature value display switching unit 111 separates the edge 65 into the edge 62, the edge 63, and the edge 64, and switches to the correlation between the feature values of the network indicated in the left part of FIG. 8.

The feature value display switching unit 111 outputs information to the result output unit 300, indicating that the number of edges representing the correlation between specific feature values has been switched. On the basis of the information supplied from the feature value display switching unit 111, indicating that the granularity of the correlation between specific feature values has been switched, the result output unit 300 displays the network in the display unit 30. The edge 65 is indicated by the edge 62, the edge 63, and the edge 64, and thus the user can confirm feature values that are correlated between the node P1 and the node P2.

Figure 10:
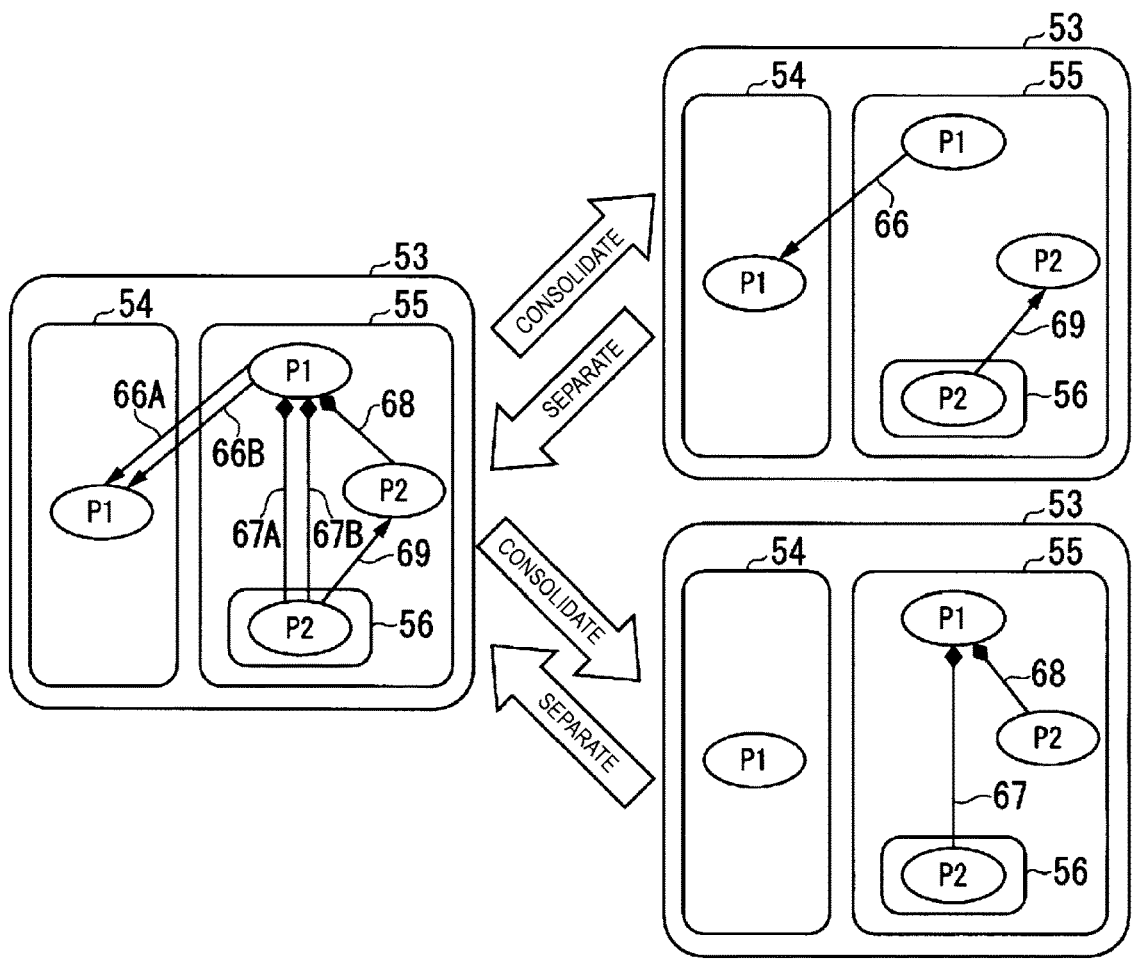
FIG. 10 is a diagram illustrating one example of a network (no. 2) of structures within a cell, output by the analysis device according to the embodiment.

FIG. 10 illustrates one example (no. 2) of a network of structures within a cell.

The left part of FIG. 10 indicates that a region 54 and a region 55 are present within a region 53, and that a region 56 is present in the region 55. Additionally, the node P1 is present in the region 54, the node P1 and the node P2 are present in the region 55, and the node P2 is present in the region 56.

Furthermore, the node P1 present in the region 54 and the node P1 present in the region 55 are connected by an edge 66A and an edge 66B indicated as progressive. Here, the node P1 present in the region 55, connected by the edge 66A and the edge 66B, is a progress origin, and the node P1 present in the region 54 is a progress destination. The node P1 and the node P2 present in the region 55 are connected by an edge 68 indicated as regressive. Here, the node P2 present in the region 55, connected by the edge 68, is a regression origin, and the node P1 present in the region 55 is a regression destination.

Furthermore, the node P1 present in the region 55 and the node P2 present in the region 56 are connected by an edge 67A and an edge 67B indicated as regressive. Here, the node P2 present in the region 56, connected by the edge 67A and the edge 67B, is a regression origin, and the node P1 present in the region 55 is a regression destination. The node P2 present in the region 55 and the node P2 present in the region 56 are connected by an edge 69 indicated as progressive. Here, the node P2 present in the region 56, connected by the edge 69, is a progress origin, and the node P2 present in the region 55 is a progress destination.

For example, a case will be described where an operation for confirming the bold edge, specifically, an operation for erasing the edge indicated as regressive and consolidating edges having equivalent orientations, has been made in the analysis device 10 in a state where the network in the left part of FIG. 10 is displayed in the display unit 30.

An operation signal representing the operation of erasing the edge indicated as regressive and consolidating edges having equivalent orientations is detected by the operation detection unit 400 and supplied to the feature value display switching unit 111 of the switching unit 105.

Upon detecting the operation signal, the feature value display switching unit 111 acquires the correlation between feature values of the network displayed in the display unit 30. Then, in accordance with the operation signal, the feature value display switching unit 111 switches the granularity of the correlation between the feature values. Specifically, the feature value display switching unit 111 erases a correlation between specific feature values and consolidates a plurality of correlations between specific feature values into a single correlation. For example, the feature value display switching unit 111 switches the correlation between the feature values in the network in which the node P1 present in the region 54 and the node P1 present in the region 55 are connected, by erasing the edge 68, the edge 67A, and the edge 67B indicated as regressive, and using an edge 66 obtained by consolidating the edge 66A and the edge 66B having equivalent orientations. This network is indicated in the upper-right part of FIG. 10.

For example, the network in the left part of FIG. 10 is displayed when an operation for confirming the feature values, specifically, an operation for displaying the edges indicated as regressive and separating the edges having equivalent orientations, has been made in the analysis device 10 in a state where the network in the upper-right part of FIG. 10 is displayed in the display unit 30.

For example, a case will be described where an operation for confirming the bold edge, specifically, an operation for erasing the edge indicated as progressive and consolidating edges having equivalent orientations, has been made in the analysis device 10 in a state where the network in the left part of FIG. 10 is displayed in the display unit 30.

An operation signal representing the operation of erasing the edge indicated as progressive and consolidating edges having equivalent orientations is detected by the operation detection unit 400 and supplied to the feature value display switching unit 111 of the switching unit 105.

Upon detecting the operation signal, the feature value display switching unit 111 acquires the correlation between feature values of the network displayed in the display unit 30. Then, in accordance with the operation signal, the feature value display switching unit 111 switches the granularity of the correlation between the feature values. Specifically, the feature value display switching unit 111 erases a correlation between specific feature values and consolidates a plurality of correlations between specific feature values into a single correlation. For example, the feature value display switching unit 111 switches the correlation between the feature values in the network in which the node P1 present in the region 55 and the node P2 present in the region 56 are connected, by erasing the edge 66A, the edge 66B, and the edge 69 indicated as progressive, and using an edge 67 obtained by consolidating the edge 67A and the edge 67B having equivalent orientations. This network is indicated in the lower-right of FIG. 10.

A case will be described where, for example, an operation for confirming the feature values, specifically, an operation for displaying (adding) an edge indicated as progressive and separating edges having equivalent orientations, has been made in the analysis device 10 in a state where the network in the lower-right part of FIG. 10 is displayed in the display unit 30.

An operation signal representing the operation of displaying the edge indicated as progressive and separating edges having equivalent orientations is detected by the operation detection unit 400 and supplied to the feature value display switching unit 111 of the switching unit 105.

Upon being supplied with the operation signal, the feature value display switching unit 111 acquires the correlation between feature values of the network displayed in the display unit 30. Then, in accordance with the operation signal, the feature value display switching unit 111 switches the granularity of the correlation between the feature values. Specifically, the feature value display switching unit 111 adds a correlation between specific feature values and separates a correlation between specific feature values into a plurality of correlations. For example, the feature value display switching unit 111 switches the granularity of the correlation between the feature values of the acquired network, and acquires the correlation between feature values of the network indicated in the left side of FIG. 10.

Additionally, in accordance with an operation signal supplied by the operation detection unit 400, the feature value display switching unit 111 carries out a switch so that different regions, which include a plurality of nodes connected by an edge, are connected. Additionally, in accordance with an operation signal supplied by the operation detection unit 400, the feature value display switching unit 111 carries out a switch so that one or more nodes present in each of a plurality of regions connected by an edge are connected on the basis of the correlation of the feature values.

Figure 11:
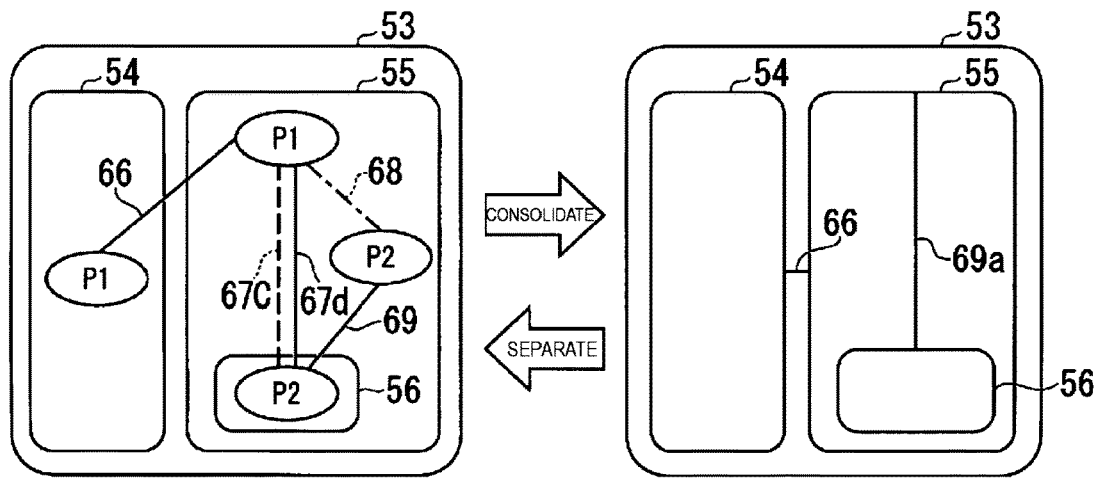
FIG. 11 is a diagram illustrating one example of a network (no. 3) of structures within a cell, output by the analysis device according to the embodiment.

FIG. 11 illustrates one example (no. 3) of a network of structures within a cell. The left part of FIG. 11 indicates that a region 54 and a region 55 are present within a region 53, and that a region 56 is present in the region 55. Additionally, the left part of FIG. 11 indicates that the node P1 is present in the region 54, the node P1 and the node P2 are present in the region 55, and the node P2 is present in the region 56.

Furthermore, the left part of FIG. 11 indicates that the node P1 present in the region 54 and the node P2 present in the region 55 are connected by the edge 66, and the node P1 and the node P2 present in the region 55 are connected by the edge 68.

Furthermore, the left part of FIG. 11 indicates that the node P1 present in the region 55 and the node P2 present in the region 56 are connected by an edge 67c and an edge 67d, and the node P2 present in the region 55 and the node P2 present in the region 56 are connected by the edge 69.

A case will be described where, for example, an operation for consolidating regions where each of a plurality of nodes connected by an edge is present has been made in the analysis device 10 in a state where the network in the left part of FIG. 11 is displayed in the display unit 30.

An operation signal representing the operation for consolidating the regions where each of a plurality of nodes is present detected by the operation detection unit 400 and supplied to the feature value display switching unit 111.

Upon being supplied with the operation signal, the feature value display switching unit 111 acquires the correlation between feature values of the network displayed in the display unit 30. Then, in accordance with the operation signal, the feature value display switching unit 111 switches the granularity of the correlation between the specific feature values. The feature value display switching unit 111 connects the region 54 and the region 55 using the edge 66, which connects the node P1 present in the region 54 and the node P1 present in the region 55, and switches to a correlation between feature values of a network in which the region 55 and the region 56 are connected by an edge 69a, which is obtained by consolidating the edge 67c and the edge 67d connecting the node P1 present in the region 55 with the node P2 present in the region 56; and the edge 69 connecting the node P2 present in the region 55 with the node P2 present region 56. This network is indicated in the right part of FIG. 11.

A case will be described where, for example, an operation for separating an edge, which connects each of a plurality of regions, into edges connecting one or more nodes present in the plurality of regions, has been made in the analysis device 10 in a state where the network in the right part of FIG. 11 is displayed in the display unit 30.

An operation signal representing the operation of separating the edge into edges connecting one or more nodes present in the plurality of regions is detected by the operation detection unit 400 and supplied to the feature value display switching unit 111 of the switching unit 105.

Upon being supplied with the operation signal, the feature value display switching unit 111 acquires the correlation between feature values of the network displayed in the display unit 30. Then, in accordance with the operation signal, the feature value display switching unit 111 switches the granularity of the correlation between the feature values. The feature value display switching unit 111 switches the correlation between the feature values of the acquired network, and acquires the correlation between feature values of the network indicated in the left side of FIG. 11. Specifically, the feature value display switching unit 111 acquires the node P1 present in the region 54, the node P1 and the node P2 present in the region 55, and the node P2 present in the region 56. Then, the feature value display switching unit 111 connects the node P1 present in the region 54 with the node P1 present in the region 55 using the edge 66; connects the node P1 and the node P2 present in the region 55 using the edge 68; connects the node P1 present in the region 55 with the node P2 present in the region 56 using the edge 67c and the edge 67d; and connects the node P2 present in the region 55 with the node P2 present in the region 56 using the edge 69.

Additionally, in accordance with the operation signal supplied by the operation detection unit 400, the feature value display switching unit 111 switches to a heat map display by using colors to represent values of the correlations between feature values of the plurality of nodes, which are indicated by edges.

Figure 12:
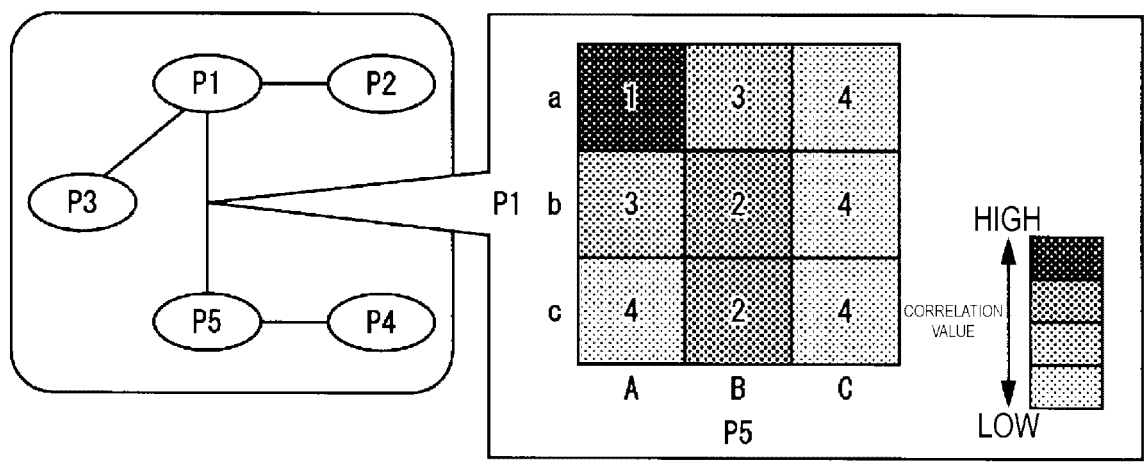
FIG. 12 is a diagram illustrating one example of a network (no. 4) of structures within a cell, output by the analysis device according to the embodiment.

FIG. 12 illustrates one example (no. 4) of a network of structures within a cell. FIG. 12 indicates that the node P1, the node P2, the node P3, a node P4, and a node P5 are present in a given region. Furthermore, FIG. 12 indicates that the node P1, the node P2, the node P3, and the node P5 are connected, and that the node P5 and the node P4 are connected.

A case will be described where, for example, an operation for confirming the value of a correlation between feature values expressed by an edge connecting the node P1 with the node P5, specifically, an operation for displaying the value of the correlation between the feature values expressed by the edge connecting the node P1 with the node P5 as a heat map, has been made in the analysis device 10 in a state where the network indicated in FIG. 12 is displayed in the display unit 30.

An operation signal representing the operation for displaying the value of the correlation between the feature values, expressed by the edge connecting the node P1 with the node P5, as a heat map is detected by the operation detection unit 400, and supplied to the feature value display switching unit 111 of the switching unit 105.

Upon detecting the operation signal, the feature value display switching unit 111 acquires the correlation between feature values of the network displayed in the display unit 30. Then, in accordance with the operation signal, the feature value display switching unit 111 carries out a switch so that the value of the correlation between the feature values, expressed by the edge connecting the node P1 with the node P5, can be displayed as a heat map. A heat map image obtained by switching the value of the correlation between the feature values is indicated in the right side of the network in FIG. 12. In this heat map display, feature values of the node P1 are indicated as "a", "b", and "c" in the vertical direction; and a feature value "A", a feature value "B", and a feature value "C" of the node P5 are indicated in the horizontal direction. The value of the correlation between the feature value of the node P1 and the feature value of the node P5 is expressed as a color of a region where the feature value of the node P1 and the feature value of the node P5 intersect.

In the example illustrated in FIG. 12, hatching is used instead of colors. As illustrated in FIG. 12, the correlation value of the region where the feature value "a" of the node P1 intersects with the feature value "A" of the node P5 is the highest, and the correlation value of the region were the feature value "a" and the feature value "b" of the node P1 intersect with the feature value "B" of the node P5 is the next highest. Furthermore, in the example illustrated in FIG. 12, the correlation value of the region where the feature value "a" of the node P1 intersects with the feature value "B" of the node P5 and the correlation value of the region where the feature value "b" of the node P1 intersects with the feature value "A" of the node P5 are the next highest; and the correlation value of the region where the feature value "a", the feature value "b", and the feature value "c" of the node P1 intersect with the feature value "C" of the node P5 and the correlation value of the region where the feature value "c" of the node P1 intersects with the feature value "A" of the node P5 are the next highest.

The descriptions will be continued, returning to FIG. 7. In accordance with an operation signal supplied by the operation detection unit 400, the position information display switching unit 112 changes the unit of the position information by changing the fineness of the regions in which a plurality of nodes connected by edges are present. The position information display switching unit 112 performs refinement by comprehensively expressing the regions in which each of the plurality of nodes connected by edges are present. Additionally, the position information display switching unit 112 performs abstraction by comprehensively expressing the regions in which each of the plurality of nodes connected by edges are present.

A specific example of the processing carried out by the position information display switching unit 112 will be described in detail below.

Figure 13:
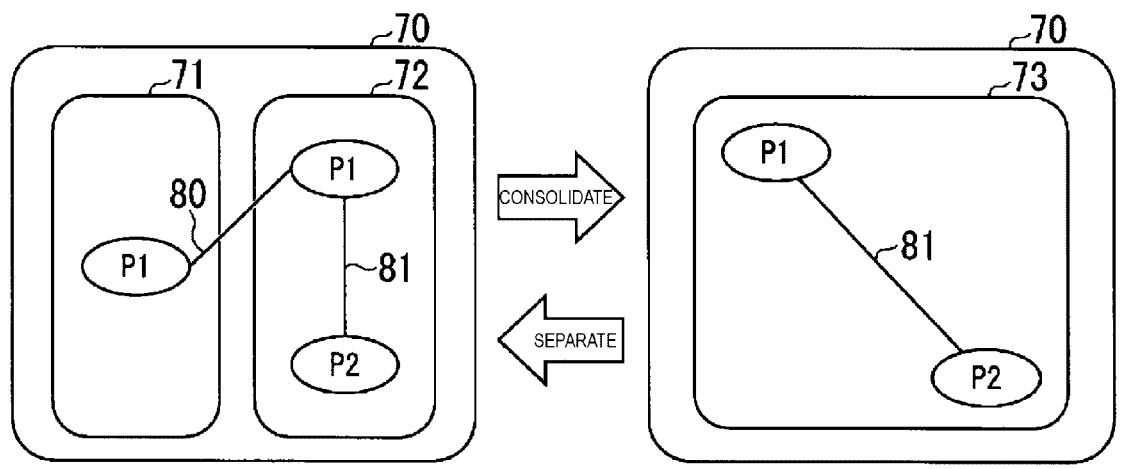
FIG. 13 is a diagram illustrating one example of a network (no. 5) of structures within a cell, output by the analysis device according to the embodiment.

FIG. 13 illustrates one example (no. 5) of a network of structures within a cell.

The left part of FIG. 13 indicates that a region 71 and a region 72 are present within a region 70, that the node P1 is present in the region 71, and that the node P1 and the node P2 are present in the region 72.

Furthermore, the left part of FIG. 13 indicates that the node P1 present in the region 71 and the node P1 present in the region 72 are connected by an edge 80, and the node P1 and the node P2 present in the region 72 are connected by an edge 81.

The right part of FIG. 13 indicates a state in which, in the left part of FIG. 13, the node P1 present in the region 71 and the node P1 present in the region 72 have been consolidated, and furthermore, the region 71 and the region 72 have been consolidated, into a region 73. A case will be described where, for example, an operation for making an abstraction of the region 71 and the region 72 has been made in the analysis device 10 in a state where the network in the left part of FIG. 13 is displayed in the display unit 30.

An operation signal representing the abstraction operation is detected by the operation detection unit 400 and supplied to the position information display switching unit 112 of the switching unit 105. The position information display switching unit 112 acquires the correlation between feature values of the network displayed in the display unit 30. Then, in accordance with the operation signal supplied from the operation detection unit 400, the position information display switching unit 112 creates the region 73 by consolidating the region 71 and the region 72, and furthermore, the feature value display switching unit 111 consolidates the node P1 present in the region 71 and the node P1 present in the region 72 into a single node P1. As a result, the switching unit 105 carries out a switch so as to create the network illustrated in the right part of FIG. 13.

Additionally, a case will be described where, for example, an operation for refining the region 73 has been made in the analysis device 10 in a state where the network in the right part of FIG. 13 is displayed in the display unit 30.

An operation signal representing the refining operation is detected by the operation detection unit 400 and supplied to the position information display switching unit 112 of the switching unit 105.

The position information display switching unit 112 acquires the correlation between feature values of the network image displayed in the display unit 30. Then, in accordance with the operation signal supplied from the operation detection unit 400, the position information display switching unit 112 carries out the refinement by separating the region 73 into the region 71 and the region 72. Furthermore, the feature value display switching unit 111 separates the node P1 present in the region 73 into P1 present in the region 71 and the node P1 present in the region 72, and connects P1 present in the region 71 with the node P1 present in the region 72 using the edge 80.

For example, in the present embodiment, the region 70 represents a cell, the region 72 represents the cell nucleus, and the region 71 represents the cytoplasm. The region 73 represents a cell. Accordingly, the left part of FIG. 13 expresses a correlation in the cytoplasm (the region 71) and a correlation in the cell nucleus (the region 72) within the cell (the region 70). The correlation between the cytoplasm (the region 71) and the cell nucleus (the region 72) is also represented. On the other hand, the right part of FIG. 13 expresses a correlation in the cell (the region 73) within the cell (the region 70). Note that in the present embodiment, although the cell (the region 70) and the cell (the region 73) are the same, the display is made to make it clear that the region 73 has been formed by the consolidation of the region 71 and the region 72. Additionally, in the present embodiment, the node P1 and the node P2 represent different types of proteins. Accordingly, in the present embodiment, different proteins (the node P1 and the node P2) are correlated within the cell (the region 73), but looking at the left part of FIG. 13, in which the fineness of the region information has been changed, it is clear that the different proteins are correlated with the cell nucleus (the region 72) in the cell (the region 73).

Although the present embodiment focuses on constituent elements of the cell, such as the nucleus and the cytoplasm, as the region information, the information is not limited thereto. For example, FIG. 13 focuses on constituent elements of the cell nucleus (the region 72) and the cytoplasm (the region 71), which are organelles within the cell (the region 73). For example, in the cell (the region 73), the positions where the node P1 and the node P2 are present may be separated. For example, whether the distance between the node P1 and the node P2 is less than 1 µm or greater than 1 µm is classified as the region 71 or the region 72. Accordingly, the region information is not limited to the type of organelle within the cell.

Figure 14:
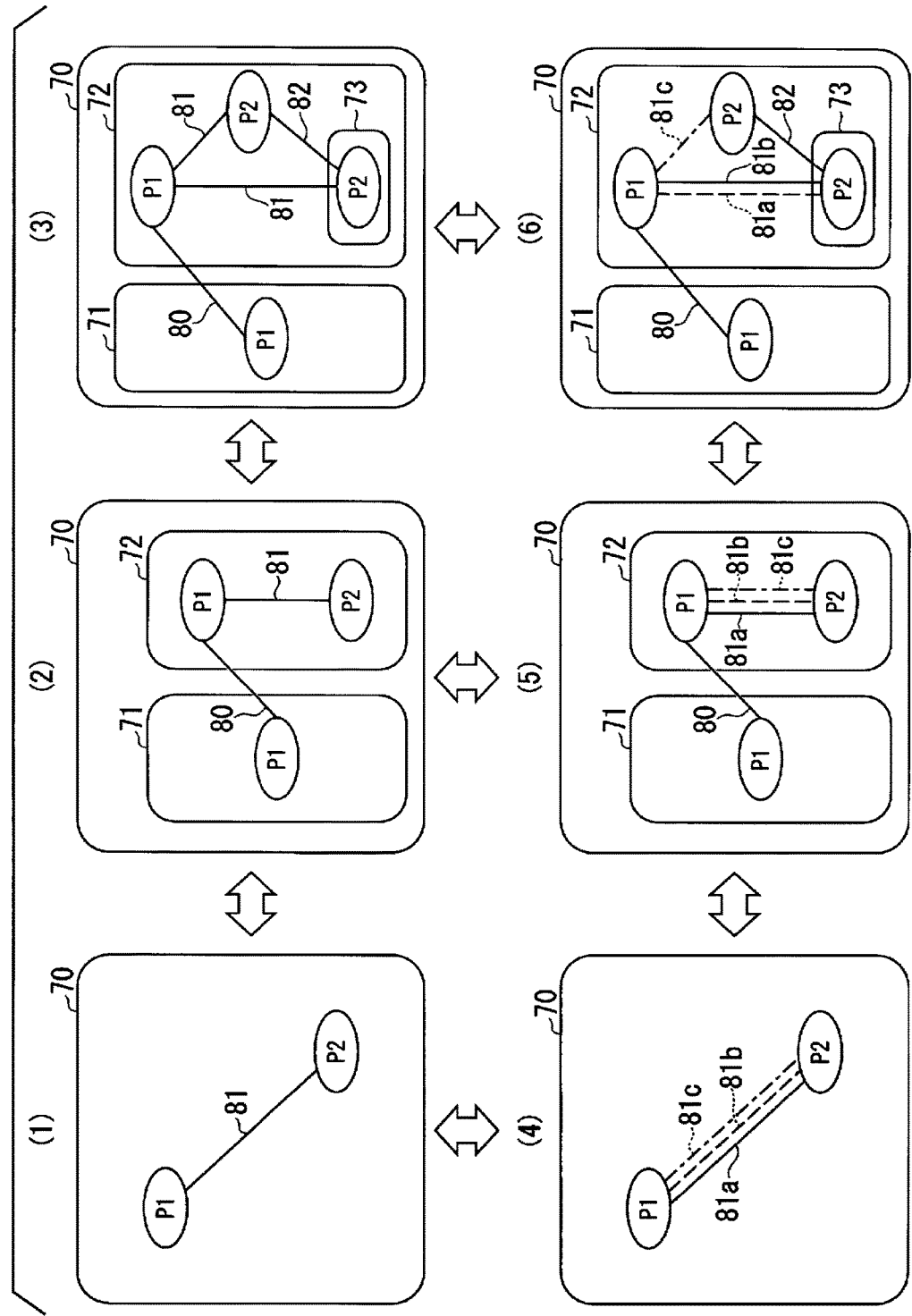
FIG. 14 is a diagram illustrating an example of network editing in the analysis device according to the embodiment.

FIG. 14 is a diagram illustrating an example of the switching of a network. For example, when the network of FIG. 14(1) or FIG. 14(4) is displayed in the display unit 30; and an operation for refining the region 70 is made in the analysis device 10, the display of the region is refined; and FIG. 14(2) or FIG. 14(5) is displayed. This makes it possible to confirm the regions where the nodes are correlated, which in turn makes it possible to estimate the mechanisms within the cell in more detail.

From the examples illustrated in FIG. 14(1) to FIG. 14(2), it can be seen that the node P1 and the node P2 indicated in FIG. 14(1) were correlated in the region 72. Likewise, from the examples illustrated in FIG. 14(4) to FIG. 14(5), it can be seen that the node P1 and the node P2 indicated in FIG. 14(4) were correlated in the region 72.

When the network of FIG. 14(2) or FIG. 14(5) is displayed; and an operation for refining the region 72 is made in the analysis device 10, the display of the region is refined; and FIG. 14(3) or FIG. 14(6) is displayed. This makes it possible to confirm the regions where the nodes are correlated, which in turn makes it possible to estimate the mechanisms within the cell in more detail. From the examples illustrated in FIG. 14(2) to FIG. 14(3), it can be seen that while FIG. 14(2) indicates that the node P1 and the node P2 are correlated in the region 72, P1 in the region 72 was also correlated with P2 in the region 73. Likewise, from the examples illustrated in FIG. 14(5) to FIG. 14(6), it can be seen that while FIG. 14(5) indicates that the node P1 and the node P2 are correlated in the region 72, P1 in the region 72 was also correlated with P2 in the region 73.

Conversely, when the network of FIG. 14(3) or FIG. 14(6) is displayed; and an operation for making an abstraction of the region 72 and the region 73 is made in the analysis device 10, the display of the region is made abstract; and FIG. 14(2) or FIG. 14(5) is displayed.

When the network of FIG. 14(2) or FIG. 14(5) is displayed; and an operation for making an abstraction of the region 71 and the region 72 is made in the analysis device 10, the display of the regions is made abstract; and FIG. 14(1) or FIG. 14(4) is displayed.

Additionally, for example, when the network image of FIG. 14(1) or FIG. 14(2) is displayed in the display unit 30; and an operation for separating the edge 81 is made in the analysis device 10, the granularity of the edges is made concrete; and FIG. 14(4) or FIG. 14(5) is displayed.

When the network image of FIG. 14(4) or FIG. 14(5) is displayed; and an operation for consolidating an edge 81a, an edge 81b, and an edge 81c is made in the analysis device 10, the granularity of the edges is made abstract; and FIG. 14(1) or FIG. 14(2) is displayed.

Additionally, for example, when the network of FIG. 14(3) is displayed in the display unit 30; and an operation for separating the edge 81 is made in the analysis device 10, the granularity of the edges is made concrete; and FIG. 14(6) is displayed. That is, the information constituting the edges is made concrete, and is based on more detailed information.

When the network of FIG. 14(6) is displayed; and an operation for consolidating the edge 81a and the edge 81b is made in the analysis device 10, the granularity of the edges is made abstract; and FIG. 14(3) is displayed.

As illustrated in FIG. 14, the analysis device according to the present embodiment can change the display of regions, the granularity of the edges, and the like in networks. Accordingly, the analysis device can assist in the understanding of biological mechanisms on the basis of the networks.

With the analysis device 10 according to the present embodiment, the switching unit 105 switches the granularity of edges representing correlations between feature values. Thus, according to the analysis device 10, the analysis can be carried out in a state where the correlations between feature values have been refined, made abstract, or the like. That is, according to the analysis device 10, when mutual effects within a cell or between cells are represented by a network, the correlations between feature values within the cells can be analyzed.

Additionally, according to the analysis device 10, the switching unit 105 refines or makes abstract the regions where nodes, which include feature values having correlations represented by edges, are present. Thus, according to the analysis device 10, the analysis can be carried out in a state where the regions where nodes are present have been refined, made abstract, or the like. That is, according to the analysis device 10, when mutual effects within a cell or between cells are represented by a network, the correlations between feature values within the cells can be analyzed.

For example, to use an example where the correlation between feature values within a cell is acquired, when acquiring the correlation between feature values within the cell, there are cases where, for example, a plurality of cells can be acquired in an image, and the correlation between feature values can be acquired in each of the plurality of cells. In this case, when the correlations between feature values in the plurality of cells are acquired, the correlations can be acquired for the plurality of cells, as compared to a case where a correlation is acquired for a single cell. This makes it possible to increase the accuracy of, for example, a signal transduction path calculated having acquired the correlations.

However, when correlations between feature values are acquired for a plurality of cells in order to increase the accuracy, the network becomes complicated. In this case, the edges representing the correlations between the feature values; the regions where nodes, which include feature values having correlations represented by edges, are present; and the like can be refined or made abstract, and thus the network can be made more understandable.

Additionally, to use an example where the correlation between cells is acquired, when acquiring the correlation between cells, there are cases where, for example, a plurality of cells can be acquired in an image, and the correlation of the cells can be acquired for that plurality of cells. In this case, there are cases where a predetermined cell correlates with a plurality of cells, and cases where a cell aside from the predetermined cell correlates with a plurality of cells. In this case, acquiring correlations of the cells among the respective cells makes it possible to increase the accuracy of, for example, signal transduction paths between the cells calculated having acquired the correlations. However, when correlations of a plurality of cells are acquired in order to increase the accuracy, the network becomes complicated. In this case, edges representing correlations between feature values; the regions where nodes, which include feature values having correlations expressed by edges, are present; and the like can be switched, which makes it possible to display the network in an easily understandable manner.

With respect to the feature values calculated by the feature value calculation unit 102, when, for example, finding the signal transduction within a cell as a correlation after the cell has received a signal from outside of the cell, the behavior of proteins contributing to the signal transduction within the cell; changes in the cell resulting therefrom; and the like may be extracted as the feature value.

That is, for example, the feature value may be the type of matter contributing to the signal transduction within the cell, or may be a change in the shape of the cell resulting from signal transduction within the cell. To specify the matter contributing to the signal transduction within the cell, NMR may be used, or a method may be employed where the partner having a mutual effect is inferred from the stain that is used.

Although the foregoing embodiment describes a case where the network displayed in the display unit 30 is switched, the present invention is not limited to this example. For example, before making a display in the display unit 30, one or both of the granularity of the correlation between specific feature values and the regions where feature values having specific correlations are present may be switched on the basis of an operation signal detected by the operation detection unit 400, after which the network may be displayed.

Although signal transduction within a cell in response to a stimulus is found in the above-described embodiment, the signal transduction within the cell may be found in an un-stimulated state.

Although the foregoing embodiment describes a case where there is correlation between nodes, the present invention is not limited to this example. For example, there may be correlation between groups which are constituted by a plurality of nodes. These groups may be called pathways. Then, the above-described processing may be carried out on the basis of a network in which these pathways are connected by edges.

The above-described various processing may be realized by recording a program for executing the processing of the analysis device 10 according to embodiments of the present invention in a computer-readable recording medium and causing a computer system to read and execute a program recorded in the recording medium.

Note that the "computer system" referred to here may include an OS and hardware such as a peripheral device.

Further, when the "computer system" uses a WWW system, this includes a homepage provision environment (or display environment). Moreover, a "computer-readable recording medium" refers to a portable medium such as a flexible disk, a magneto-optical disk, a ROM, a writable non-volatile memory such as a flash memory, or a CD-ROM; or a storage device such as a hard disk that is built into the computer system.

Further, the "computer-readable recording medium" may also include a medium that holds the program for a certain period of time, such as a volatile memory (DRAM (Dynamic Random Access Memory), for example) built into a computer system that is a server or a client when the program is transmitted over a network such as the Internet or a communication line such as a phone line. In addition, the above-described program may be transmitted, from the computer system in which the program is stored in a storage device or the like, to another computer system, via a transmission medium or by transmission waves in the transmission medium. Here, the "transmission medium" that transmits the program refers to a medium having a function to transmit information, such as the Internet or another network (communication network), and a communication line such as a telephone line. Further, the above-described program may be a program for realizing a part of the above-described functions. Moreover, the above-described functions may be realized by a combination with a program already recorded in the computer system, namely, by a so-called differential file (differential program).

Although embodiments of the present invention have been described in detail above with reference to the drawings, the specific configuration is not limited to the embodiments, and designs and the like within the scope of the present invention are included.

Note that the elements in the above-described embodiments can be combined as appropriate. Moreover, some of the constituent elements may be omitted. Moreover, to the extent permissible by law, all publications and the US patent documents related to the devices or the like used in the embodiments and modification examples as described above are incorporated herein by reference.

REFERENCE SIGNS LIST 1 microscope observation system
10 analysis device
20 microscope device
21 electromotive stage
22 image capturing unit
30 display unit
100 computation unit
101 cell image acquisition unit
102 feature value calculation unit
103 noise component removal unit
104 correlation extraction unit
105 switching unit
106 correlation calculation unit
107 position information calculation unit
200 storage unit
201 type storage unit
202 experiment condition storage unit
300 result output unit
400 operation detection unit

What is claimed is:

1. An analysis device configured to analyze a correlation between constituent elements, based on one or more types of feature values, for each of the constituent elements of a cell that has been stimulated, the device comprising:
   a feature value calculation unit configured to calculate the feature value for each of the constituent elements of the cell from cell images in which an image of the cell has been captured;
   a correlation calculation unit configured to calculate correlations between the constituent elements of the cell from the feature values calculated by the feature value calculation unit;
   a position information specifying unit configured to specify a position information at which the constituent elements are present;
   a display unit configured to display the correlation between the constituent elements based on the position information specified by the position information specifying unit; and
   a position information display switching unit configured to switch the position information at which the constituent elements are displayed,
   wherein the display unit switches the display of the correlation of the constituent elements in accordance with the switching of the position information.

2. The analysis device according to claim 1,
   wherein the position information display switching unit switches the display pertaining to the display of the position information.

3. The analysis device according to claim 2, further comprising
   a correlation extraction unit configured to extract first and second feature values for each of the constituent elements from the cell images, wherein
   the correlation extraction unit is configured to extract correlations between the first feature values and between the second feature values,
   the correlation between the first feature values is extracted by selecting the first feature values with respect to the correlations between the constituent elements calculated by the correlation calculation unit, and
   the display unit displays the correlation calculated between the first feature values.

4. The analysis device according to claim 3, further comprising
   a feature value display switching unit configured to switch the display of the correlation between the feature values in the constituent elements,
   wherein the feature value display switching unit switches the display of the correlation between the first feature values to the correlation between the second feature values by selecting the second feature values.

5. The analysis device according to claim 3, wherein
   the display of the correlation between the first feature values is the display of the correlation between feature values which are obtained by consolidating a plurality of types of correlations, and
   the display of the correlation between the second feature values is the display of the correlation between feature values which are obtained by separating the consolidation of the plurality of types of correlations.

6. The analysis device according to claim 3, wherein
   the display of the correlation between the first feature values is the display of the correlation between feature values which are obtained by consolidating a plurality of correlations, and
   the display of the correlation between the second feature values is the display of the correlation between feature values which are obtained by separating the consolidation of the plurality of correlations.

7. The analysis device according to claim 4, wherein the feature value display switching unit erases the correlation between the first feature values of the constituent elements.

8. The analysis device according to claim 7, wherein the feature value display switching unit can again display the correlation between the first feature values that has been erased.

9. The analysis device according to claim 1, wherein the feature values for each of the constituent elements are different types of feature values.

10. The analysis device according to claim 1, wherein the feature values of the constituent elements include either or both of luminosity information found from the cell image and shape information of the constituent elements.

11. The analysis device according to claim 1, further comprising:
a cell image acquisition unit configured to acquire a plurality of the cell images of the stimulated cell.

12. An analysis method executed by an analysis device that analyzes a correlation between constituent elements, based on one or more types of feature values, for each of the constituent elements of a cell that has been stimulated, the method comprising:
calculating the feature value for each of the constituent elements of the cell from cell images in which an image of the cell has been captured;
calculating correlations between the constituent elements of the cell from the feature values that have been calculated;
specifying a position information at which the constituent elements are present;
displaying the correlation of the constituent elements based on the position information that has been specified; and
switching the position information at which the constituent elements are displayed,
wherein the displaying switches the display of the correlation between the constituent elements in accordance with the switching of the position information.

13. A non-transitory computer-readable recording medium on which is stored a program that, when executed by a computer of an analysis device that analyzes a correlation between constituent elements, based on one or more types of feature values, for each of the constituent elements of a cell that has been stimulated, causes the computer to perform the steps of:
calculating the feature value for each of the constituent elements of the cell from cell images in which an image of the cell has been captured;
calculating correlations between the constituent elements of the cell from the feature values that have been calculated;
specifying a position information at which the constituent elements are present;
displaying the correlation of the constituent elements based on the position information that has been specified; and
switching the position information at which the constituent elements are displayed,
wherein the displaying switches the display of the correlation between the constituent elements in accordance with the switching of the position information.

* * * * *